(12) United States Patent
Edgell et al.

(10) Patent No.: US 8,972,021 B2
(45) Date of Patent: Mar. 3, 2015

(54) DETACHABLE HELICAL ANTENNA FOR IMPLANTABLE MEDICAL DEVICE

(75) Inventors: John M. Edgell, Shoreview, MN (US); Lawrence D. Swanson, White Bear Lake, MN (US); Timothy J. Christman, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 813 days.

(21) Appl. No.: 12/397,180

(22) Filed: Mar. 3, 2009

(65) Prior Publication Data

US 2009/0228074 A1  Sep. 10, 2009

Related U.S. Application Data

(60) Provisional application No. 61/033,535, filed on Mar. 4, 2008.

(51) Int. Cl.
| | |
|---|---|
| A61N 1/02 | (2006.01) |
| A61N 1/372 | (2006.01) |
| H01Q 1/27 | (2006.01) |
| H01Q 1/36 | (2006.01) |
| H01Q 1/40 | (2006.01) |
| H01Q 5/00 | (2006.01) |
| H01Q 9/04 | (2006.01) |
| H01Q 11/08 | (2006.01) |
| A61B 5/00 | (2006.01) |

(52) U.S. Cl.
CPC ............ *A61N 1/37229* (2013.01); *H01Q 1/273* (2013.01); *H01Q 1/36* (2013.01); *H01Q 1/40* (2013.01); *H01Q 5/0034* (2013.01); *H01Q 5/0072* (2013.01); *H01Q 9/0471* (2013.01); *H01Q 11/083* (2013.01); *A61B 5/7203* (2013.01); *A61B 5/0031* (2013.01)

USPC .......................................................... 607/60

(58) Field of Classification Search
None
See application file for complete search history.

(56) References Cited

U.S. PATENT DOCUMENTS

| | | | | |
|---|---|---|---|---|
| 2,611,868 | A | * | 9/1952 | Marston et al. ............... 343/843 |
| 3,944,722 | A | * | 3/1976 | Larsen ...................... 174/153 A |
| 4,134,120 | A | * | 1/1979 | DeLoach et al. .............. 343/715 |
| 5,134,419 | A | | 7/1992 | Egashira |
| 5,246,438 | A | | 9/1993 | Langberg |
| 5,258,765 | A | | 11/1993 | Dorrie et al. |
| 5,364,392 | A | | 11/1994 | Warner et al. |

(Continued)

FOREIGN PATENT DOCUMENTS

| | | |
|---|---|---|
| EP | 0505673 A1 | 9/1992 |
| EP | 1537895 A1 | 6/2005 |

(Continued)

OTHER PUBLICATIONS

Ameri, M., "Implantable Multi-length Antenna", U.S. Appl. No. 12/397,199, filed Mar. 3, 2009, 54 pgs.

(Continued)

*Primary Examiner* — Kennedy Schaetzle
(74) *Attorney, Agent, or Firm* — Schwegman Lundberg & Woessner, P.A.

(57) ABSTRACT

A system and method wirelessly transfers information electromagnetically using a detachable helical antenna. In an example, the detachable helical antenna can include a first threaded portion. In an example, the detachable helical antenna can be configured to mechanically threadably engage an implantable medical device.

20 Claims, 24 Drawing Sheets

(56) References Cited

U.S. PATENT DOCUMENTS

| | | | |
|---|---|---|---|
| 5,861,019 A | 1/1999 | Sun et al. | |
| 6,009,350 A | 12/1999 | Renken | |
| 6,046,707 A * | 4/2000 | Gaughan et al. | 343/895 |
| 6,115,636 A | 9/2000 | Ryan | |
| 6,167,312 A * | 12/2000 | Goedeke | 607/60 |
| 6,169,925 B1 | 1/2001 | Villaseca et al. | |
| 6,205,358 B1 | 3/2001 | Haeg et al. | |
| 6,320,545 B1 | 11/2001 | Nagumo et al. | |
| 6,456,256 B1 | 9/2002 | Amundson et al. | |
| 6,505,072 B1 * | 1/2003 | Linder et al. | 607/32 |
| 6,563,476 B1 | 5/2003 | Sheng-Gen | |
| 6,574,510 B2 | 6/2003 | Von Arx et al. | |
| 6,614,406 B2 | 9/2003 | Amundson et al. | |
| 6,708,065 B2 | 3/2004 | Von Arx et al. | |
| 6,804,561 B2 | 10/2004 | Stover | |
| 6,809,701 B2 | 10/2004 | Amundson et al. | |
| 6,823,218 B2 | 11/2004 | Berube | |
| 6,868,288 B2 | 3/2005 | Thompson | |
| 6,888,514 B2 | 5/2005 | Sheng-Gen et al. | |
| 7,016,733 B2 | 3/2006 | Dublin et al. | |
| 7,047,076 B1 * | 5/2006 | Li et al. | 607/36 |
| 7,072,718 B2 | 7/2006 | Von Arx et al. | |
| 7,149,578 B2 | 12/2006 | Edvardsson | |
| 7,289,855 B2 | 10/2007 | Nghiem et al. | |
| 7,309,262 B2 | 12/2007 | Zart et al. | |
| 7,313,441 B2 | 12/2007 | Mass et al. | |
| 7,317,946 B2 | 1/2008 | Twetan et al. | |
| 7,319,901 B2 * | 1/2008 | Dublin et al. | 607/36 |
| 7,363,087 B2 | 4/2008 | Nghiem et al. | |
| 7,392,091 B2 * | 6/2008 | Bruinsma | 607/60 |
| 7,483,752 B2 | 1/2009 | Von Arx et al. | |
| 7,903,043 B2 | 3/2011 | Prashant et al. | |
| 8,170,680 B2 | 5/2012 | Ameri | |
| 8,588,924 B2 | 11/2013 | Dion | |
| 8,619,002 B2 * | 12/2013 | Rawat et al. | 343/873 |
| 2001/0034543 A1 | 10/2001 | Haeg | |
| 2002/0065539 A1 | 5/2002 | Von Arx et al. | |
| 2002/0095195 A1 | 7/2002 | Mass et al. | |
| 2002/0123776 A1 | 9/2002 | Von Arx et al. | |
| 2002/0190916 A1 | 12/2002 | Makino | |
| 2003/0014091 A1 | 1/2003 | Rastegar et al. | |
| 2003/0018246 A1 | 1/2003 | Govari et al. | |
| 2003/0025645 A1 | 2/2003 | Amundson et al. | |
| 2003/0114897 A1 | 6/2003 | Von Arx et al. | |
| 2003/0117340 A1 | 6/2003 | Sheng-Gen et al. | |
| 2003/0195589 A1 | 10/2003 | Von Arx et al. | |
| 2004/0027306 A1 * | 2/2004 | Amundson et al. | 343/873 |
| 2004/0095289 A1 | 5/2004 | Bae et al. | |
| 2004/0176811 A1 | 9/2004 | Von Arx et al. | |
| 2005/0113886 A1 | 5/2005 | Fischell et al. | |
| 2005/0134520 A1 | 6/2005 | Rawat et al. | |
| 2005/0203583 A1 | 9/2005 | Twetan et al. | |
| 2005/0203584 A1 | 9/2005 | Twetan et al. | |
| 2005/0222633 A1 | 10/2005 | Edvardsson | |
| 2006/0089682 A1 | 4/2006 | Kronich et al. | |
| 2006/0095093 A1 | 5/2006 | Bettesh et al. | |
| 2006/0224206 A1 | 10/2006 | Dublin | |
| 2006/0247711 A1 | 11/2006 | Verhoef et al. | |
| 2006/0247712 A1 | 11/2006 | Fuller et al. | |
| 2006/0287693 A1 | 12/2006 | Kraft et al. | |
| 2007/0119741 A1 | 5/2007 | Wenger et al. | |
| 2007/0142829 A1 | 6/2007 | Ahn | |
| 2007/0179554 A1 | 8/2007 | Iyer et al. | |
| 2007/0182648 A1 * | 8/2007 | Shimamori et al. | 343/702 |
| 2007/0222697 A1 | 9/2007 | Caimi et al. | |
| 2007/0260294 A1 | 11/2007 | Schulman et al. | |
| 2007/0288065 A1 | 12/2007 | Christman et al. | |
| 2007/0288066 A1 * | 12/2007 | Christman et al. | 607/60 |
| 2008/0021522 A1 | 1/2008 | Verhoef et al. | |
| 2008/0039898 A1 | 2/2008 | Lim et al. | |
| 2009/0192574 A1 | 7/2009 | Von Arx et al. | |
| 2009/0228075 A1 | 9/2009 | Dion | |
| 2009/0228076 A1 | 9/2009 | Ameri | |

FOREIGN PATENT DOCUMENTS

| | | |
|---|---|---|
| EP | 1362614 B1 | 3/2008 |
| EP | 2266164 B1 | 5/2014 |
| EP | 2263283 B1 | 7/2014 |
| JP | 3-003824 A | 1/1991 |
| JP | 3-159402 A | 7/1991 |
| JP | 2000-59130 A | 2/2000 |
| JP | 2001-068917 A | 3/2001 |
| JP | 2004-080713 A | 3/2004 |
| JP | 2004-193774 A | 7/2004 |
| JP | 2006-130322 A | 5/2006 |
| WO | WO-98/48895 A1 | 11/1998 |
| WO | WO-00/16439 A2 | 3/2000 |
| WO | WO-0066220 A1 | 11/2000 |
| WO | WO-02/31909 A1 | 4/2002 |
| WO | WO-03/053515 A1 | 7/2003 |
| WO | WO-2005/123186 | 12/2005 |
| WO | WO-2005/123186 A1 | 12/2005 |
| WO | WO-2006/060750 A1 | 6/2006 |
| WO | WO-2006/104847 A1 | 10/2006 |
| WO | WO-2006/131302 A1 | 12/2006 |
| WO | WO-2009/111009 A1 | 9/2009 |
| WO | WO-2009/111012 A1 | 9/2009 |

OTHER PUBLICATIONS

Basset, P., et al., ""Chip-Size" Antennas for Implantable Sensors and Smart Dust", *The 13th International Conference on Solid-State Sensors, Actuators and Microsystems, Digest of Technical Papers, Transducers '05*, (Seoul, Korea, Jun. 5-9, 2005), (2005), 457-460.

Dion, P. G., "Loaded RF Antenna for Implantable Device", U.S. Appl. No. 12/397,187, filed Mar. 3, 2009, 56 pgs.

Gosalia, K., et al., "Investigation of a Microwave Data Telemetry Link for a Retinal Prosthesis", *IEEE Transactions on Microwave Theory and Techniques*, 52(8), (2004), 1925-1933.

Gosalia, K., "Novel Compact Antennas for Biomedical Implants and Wireless Applications", *Dissertation, PhD, Electrical Engineering*, Graduate Faculty of North Carolina State University, (2004), 172 pgs.

Jacobsen, S., et al., "Characteristics of Microstrip Muscle-Loaded Single-Arm Archimedean Spiral Antennas as Investigated by FDTD Numerical Computations", *IEEE Transactions on Biomedical Engineering*, 52(2), (2005), 321-330.

Johansson, A. J., "Performance Measures of Implant Anteannas", *First European Conference on Antennas and Propagation (EuCAP 2006 )*, (Nice, France, Nov. 6-10, 2006), (2006), 1-4.

Karacolak, T., et al., "Design of a Dual-Band Implantable Anteanna and Development of Skin Mimicking Gels for Continuous Glucose Monitoring", *IEEE Transactions on Microwave Theory and Techniques*, 56(4), (Apr. 2008), 1001-1008.

Kim, J., et al., "An Implanted Antenna in the Spherical Human Head: SAR and Communication Link Performance", *IEEE Topical Conference on Wireless Communication Technology*, (2003), 202-203.

Kim, J., et al., "Implanted Anteannas Inside a Human Body: Simulations, Designs, and Chararcterizations", *IEEE Transactions on Microwave Theory and Techniques*, 52(8), (2004), 1934-1943.

Ma, L., et al., "A Wearable Flexible Multi-Band Antenna Based on a Square Slotted Printed Monopole", *2008 Loughborough Antennas & Propagation Conference (LAPC 2008 )*, (Mar. 17-18, 2008, Loughborough, United Kingdom), (2008), 345-348.

Neirynck, D., et al., "Exploiting Multiple-Input Multiple-Output in the Personal Sphere", *IEt Microwaves, Antennas & Propagaton*, 1(6), (2007), 1170-1176.

Von Arx, J. A., et al., "Antenna for an Implantable Medical Device", U.S. Appl. No. 12/359,739, filed Jan. 26, 2009, 16 pgs.

"U.S. Appl. No. 09/798,249, Non Final Office Action mailed Mar. 28, 2003", 7 pgs.

"U.S. Appl. No. 09/798,249, Notice of Allowance mailed Oct. 21, 2003", 5 pgs.

"U.S. Appl. No. 09/798,249, Response filed Jul. 28, 2003 to Non Final Office Action mailed Mar. 28, 2003", 8 pgs.

"U.S. Appl. No. 10/800,596, Final Office Action mailed Mar. 7, 2007", 7 pgs.

(56) References Cited

OTHER PUBLICATIONS

"U.S. Appl. No. 10/800,596, Final Office Action mailed Dec. 4, 2007", 4 pgs.
"U.S. Appl. No. 10/800,596, Non Final Office Action mailed Mar. 3, 2008", 9 pgs.
"U.S. Appl. No. 10/800,596, Non Final Office Action mailed Jun. 28, 2007", 6 pgs.
"U.S. Appl. No. 10/800,596, Response filed Feb. 4, 2008 to Final Office Action mailed Dec. 4, 2007", 6 pgs.
"U.S. Appl. No. 10/800,596, Response filed Jun. 3, 2008 to Non-Final Office Action mailed Mar. 3, 2008", 8 pgs.
"U.S. Appl. No. 10/800,596, Response filed Jun. 7, 2007 to Final Office Action mailed Mar. 7, 2007", 8 pgs.
"U.S. Appl. No. 10/800,596, Response filed Sep. 28, 2007 to Non Final Office Action mailed Jun. 28, 2007", 8 pgs.
"U.S. Appl. No. 12/397,187, Response filed Aug. 15, 2012 to Final Office Action mailed Jun. 20, 2012", 14 pgs.
"U.S. Appl. No. 12/397,187, Response filed Oct. 15, 2012 to Final Office Action mailed Jun. 20, 2012", 12 pgs.
"U.S. Appl. No. 12/397,187, Advisory Action mailed Aug. 29, 2012", 6 pgs.
"U.S. Appl. No, 12/397,187, Examiner Interview Summary mailed Sep. 28, 2012", 3 pgs.
"U.S. Appl. No. 12/397,187, Final Office Action mailed Jun. 20, 2012", 16 pgs.
"U.S. Appl. No. 12/397,187, Non Final Office Action mailed Oct. 3, 2011", 10 pgs.
"U.S. Appl. No. 12/397,187, Response fiied Mar. 29, 2012 to Non Final Office Action mailed Oct. 3, 2011", 15 pgs.
"U.S. Appl. No. 12/397,199, Non Final Office Action mailed Apr. 21, 2011", 8 pgs.
"U.S. Appl. No. 12/397,199, Notice of Allowance mailed Jan. 5, 2012", 8 pgs.
"U.S. Appl. No. 12/397,199, Notice of Allowance mailed Sep. 23, 2011", 9 pgs.
"Australian Application Serial No. 2009220198, First Examiners Report mailed May 16, 2012", 2 pgs.
"Australian Application Serial No. 2009220201, First Examiners Report mailed Mar. 28 2012", 2 pgs.
"Australian Application Serial No. 2009220201, Response filed Oct. 12, 2012 to First Examiners Report mailed Mar. 28, 2012", 5 pgs.
"European Application Serial No. 09716210.1, Office Action mailed Nov. 4, 2010", 1 pg.
"European Application Serial No. 09716210.1, Response filed Dec. 13, 2010 to Office Action mailed Nov. 4, 2010", 17 pgs.
"European Application Serial No. 09717702.6, Office Action mailed Oct. 21, 2010", 2 pgs.
"European Application Serial No. 09717702.6, Response filed Nov. 30, 2010 to Office Action mailed Oct. 21, 2010", 15 pgs.
"International Application Seriai No. PCT/US2009/001349, International Preliminary Report on Patentability mailed Sep. 16, 2010", 8 pgs.
"International Application Serial No. PCT/US2009/001349, International Search Report mailed May 20, 2009", 5 pgs.
"International Application Serial No. PCT/US2009/001349, Written Opinion mailed May 20, 2009", 7 pgs.
"International Application Serial No. PCT/US2009/001349, International Preliminary Report on Patentability mailed Sep. 16, 2010", 8 pgs.
"Japanese Application Serial No. 2010-548748, Office Action mailed Jul. 3, 2012", (w/English Translation), 6 pgs.
"Japanese Application Serial No. 2010-548748, Office Action mailed Oct. 4, 2011", (w/English Translation), 5 pgs.
"Japanese Application Serial No. 2010-548748, Response filed Apr. 4, 2012 to Office Action mailed Oct. 4, 2011", (w/English Translation of Claims), 11 pgs.
"Japanese Application Serial No. 2010-549652, Office Action mailed Oct. 4, 2011", (w/English Translation), 6 pgs.
"Japanese Application Serial No. 2010-549652, Response filed Apr. 4, 2012 to Office Action mailed Oct. 4, 2011", (w/Engiish Translation of Amended Claims), 8 pgs.
"U.S. Appl. No. 12/397,199, Response filed Jul. 19, 2011 to Non-Final Office Action mailed Apr. 21, 2011", 12 pgs.
"International Application Serial No. PCT/US2009/001354, International Search Report mailed May 20, 2009", 5 pgs.
"International Application Serial No. PCT/US2009/001354, Written Opinion mailed May 20, 2009", 7 pgs.
"U.S. Appl. No. 12/397,187, Notice of Allowance mailed Jun. 14, 2013", 14 pgs.
"U.S. Appl. No. 12/397,187, Non Final Office Action mailed Nov. 5, 2012", 14 pgs.
"U.S. Appl. No. 12/397,187, Response filed Apr. 23, 2013 to Non Final Office Action mailed Nov. 5, 2012", 14 pgs.
"Australian Application No. 2009220201, Examination Report No. 2, Dated Oct. 23, 2012", 3 pgs.
"Australian Application Serial No. 2009220201, Subsequent Examiner Report mailed Jan. 3, 2013", 3 pgs.
"Australian Patent Application No. 2009220198, Response Filed Nov. 1, 2012", 2 pgs.
"European Application Serial No. 09716210.1, Office Action mailed Jan. 28, 2013", 6 pgs.
"European Application Serial No. 09717702.6, Office Action mailed Jan. 28, 2013", 6 pgs.

\* cited by examiner

TOP VIEW

SIDE VIEW

ALTERNATE

US 8,972,021 B2

DETACHABLE HELICAL ANTENNA FOR IMPLANTABLE MEDICAL DEVICE

CROSS REFERENCE TO RELATED APPLICATIONS

This patent application claims the benefit of priority, under 35 U.S.C. Section 119(e), to Greg Carpenter et al., U.S. Provisional Patent Application Ser. No. 61/033,535, entitled "ANTENNA FOR IMPLANTABLE MEDICAL DEVICE," filed on Mar. 4, 2008, incorporated herein by reference in its entirety.

BACKGROUND

Medical devices can be implanted in a body to perform tasks including monitoring, detecting, or sensing physiological information in the body, diagnosing a physiological condition or disease, treating a physiological condition or disease, or restoring or otherwise altering the function of an organ or a tissue. Examples of an implantable medical device can include a cardiac rhythm management device, such as a pacemaker, a cardiac resynchronization therapy device, a cardioverter or defibrillator, a neurological stimulator, a neuromuscular stimulator, or a drug delivery system. Implantable medical devices can include a telemetry circuit configured to provide wireless communication between the implantable medical device and an external device, e.g., to send information (such as physiological information) from the implantable medical device to the external device, or to receive information (e.g., such as programming instructions) at the implantable medical device from the external device.

OVERVIEW

This document discusses, among other things, systems and methods for wirelessly transferring information electromagnetically using a detachable helical antenna. In an example, the detachable helical antenna can include a first threaded portion. In an example, the detachable helical antenna can be configured to mechanically attach to an implantable medical device at least in part using the first threaded portion.

The present inventor has recognized, among other things, that it can be advantageous to provide a telemetry circuit or antenna for an implantable medical device that is one or more of adaptable, compact in size, efficient, that increases a communication range, suitable for providing communication over various media (e.g., tissue, air, etc.), or otherwise increases the abilities or options for communication between an implantable device and an external device or between multiple implantable devices.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
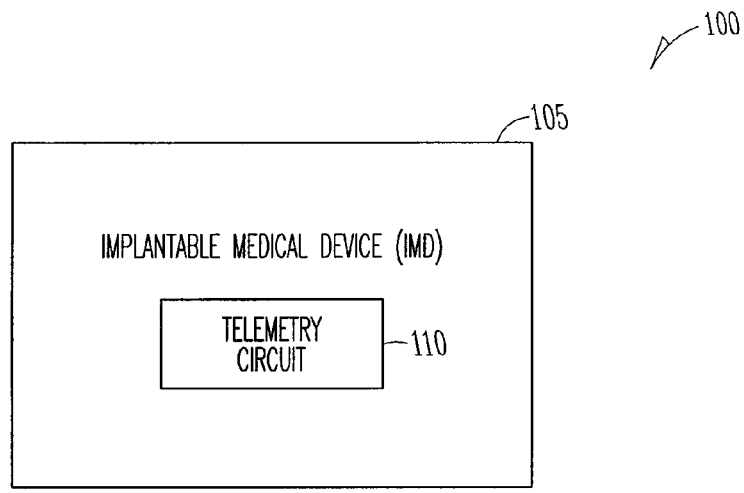
FIG. 1 illustrates generally an example of a system including an implantable medical device (IMD) having a telemetry circuit.

FIG. 1 illustrates generally an example of a system 100 including an implantable medical device (IMD) 105 having a telemetry circuit 110. In an example, the IMD 105 can include a medical device configured to be implanted in a body. In certain examples, the IMD 105 can be implanted in the body, or the IMD 105 can be capable of being implanted, but can reside outside the body (e.g., the IMD 105 can operate in air outside of the body, such as before being implanted in the body or after being explanted from the body).

In an example, the telemetry circuit 110 can be configured to provide far-field telemetry with another medical device, such as an external medical device. In certain examples, the telemetry circuit 110 can include at least one of an antenna, a receiver, a transmitter, or an energy source. In certain examples, at least a portion of the telemetry circuit 110 (e.g., the antenna, for example) can come into contact with biological material (e.g., skin, tissue, body fluid, etc.). Thus, at least a portion of the telemetry circuit 110 (e.g., the portion that can come into contact with biological material) can be made or manufactured using one or more biocompatible materials, or materials that can be safely implanted in the body.

In an example, the receiver can include an amplifier, a demodulator, or other receiver circuit. In an example, the transmitter can include an amplifier, a modulator, a radio frequency (RF) carrier generator, or other transmitter circuit. In certain examples, the telemetry circuit 110 can include a transceiver, including both a transmitter and a receiver.

Figure 2:
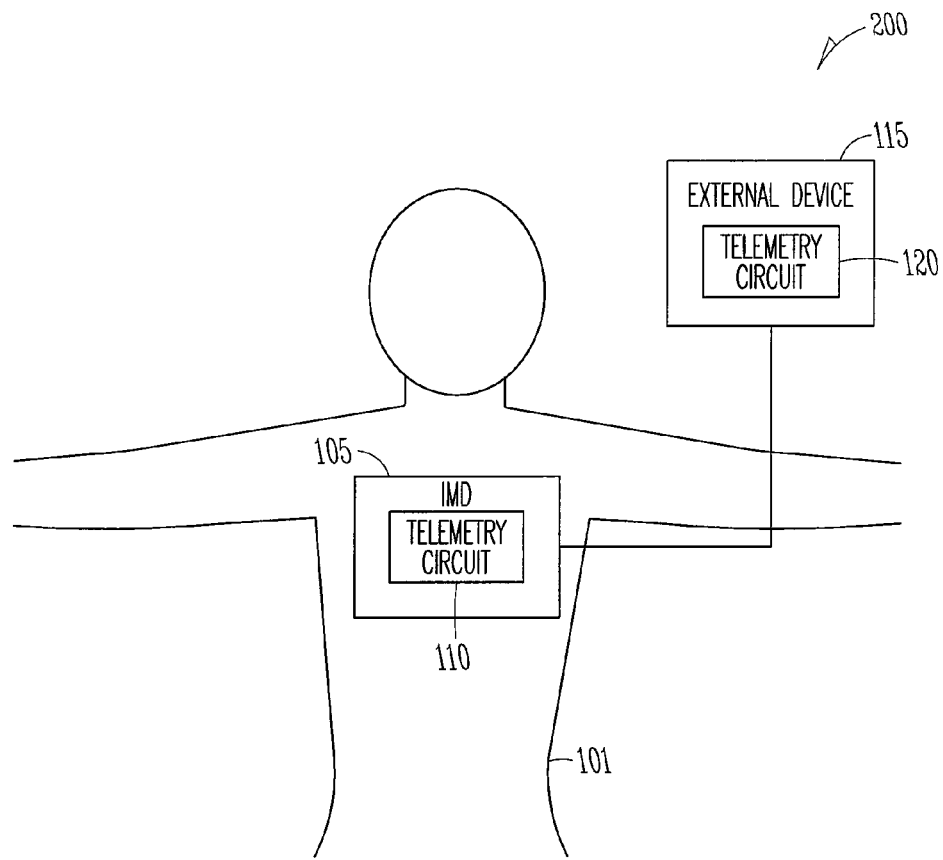
FIG. 2 illustrates generally an example of a system including an IMD and an external device.

FIG. 2 illustrates generally an example of a system 200 including an IMD 105 and another device, such as an external device 115. In certain examples, the IMD 105 can include a telemetry circuit 110, or the external device 115 can include a telemetry circuit 120. In an example, the IMD 105 can be communicatively coupled, such as by using wireless telemetry, to the external device 115.

In the example of FIG. 2, the IMD 105 can be implanted in a subject 101, and can be communicatively coupled to an external device 115 located outside the body. In certain examples, the IMD 105 can be configured to be implanted in the body, but can be located outside of the body, such as before implant or after explant, for example. In that example, the IMD 105 can be an externally-located component that can be communicatively coupled to the external device 115.

Figure 3:
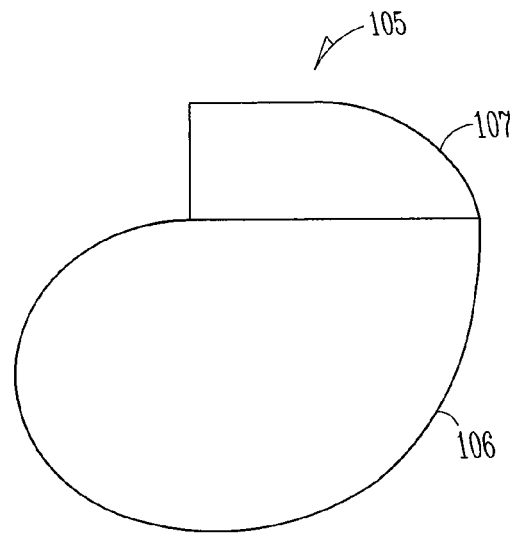
FIGS. 3-5 illustrate generally an example of an IMD including a housing and a header.

FIG. 3 illustrates generally an example of an IMD 105 including a housing 106 and a header 107. In an example, the housing 106 can include within an energy delivery circuit, a physiological information detector circuit, a controller, or other implantable medical device circuit. In an example, the exterior of the housing 106 (also referred to as a "case" or a "can") can include a conductive material, such as titanium or other conductive biocompatible material. In certain examples, the exterior of the housing 106 can include other non-conductive biocompatible material, such as ceramic. In an example, the header 107 can include a receptacle, e.g., to receive an intravascular or other lead, an electrode, or other component. In an example, the header 107 can be formed at least in part by using an insulative or non-conductive material, such as molded plastic. In certain examples, the header 107 can be substantially transparent, at least in part, such as to include a line-of-sight to at least a portion of the receptacle (e.g., the portion of the receptacle where the lead or the electrode is received) so that a user can visually verify a correct placement of the lead or electrode in the receptacle.

In an example, at least a portion of the telemetry circuit 110 (e.g., the antenna), can be located at least in part inside or on the housing 106, inside or on the header 107, outside the housing 106 or the header 107, or any combination or permutation of inside or on the housing 106, inside or on the header 107, or outside the housing 106 or the header 107. For example, an energy source, a receiver, or a transmitter can be located inside of the housing 106, while the antenna can be located entirely within the header 107. In certain examples, at least a portion of the antenna (e.g., at least a portion of the radiating part of the antenna, such as to avoid shielding in an example in which the housing 106 is conductive) can be located in or on the header 107, while the remainder of the antenna can be located outside of the housing 106 or the header 107 (e.g., at least a portion of the antenna can attach to the header 107 through a receptacle, for example, similar to that used to attach a lead), or while the remainder of the antenna can be located in or on the housing 106. In certain examples, the energy source, the receiver, or the transmitter can be located outside of the header or the housing.

Antenna Threaded Into IMD

Figure 4:
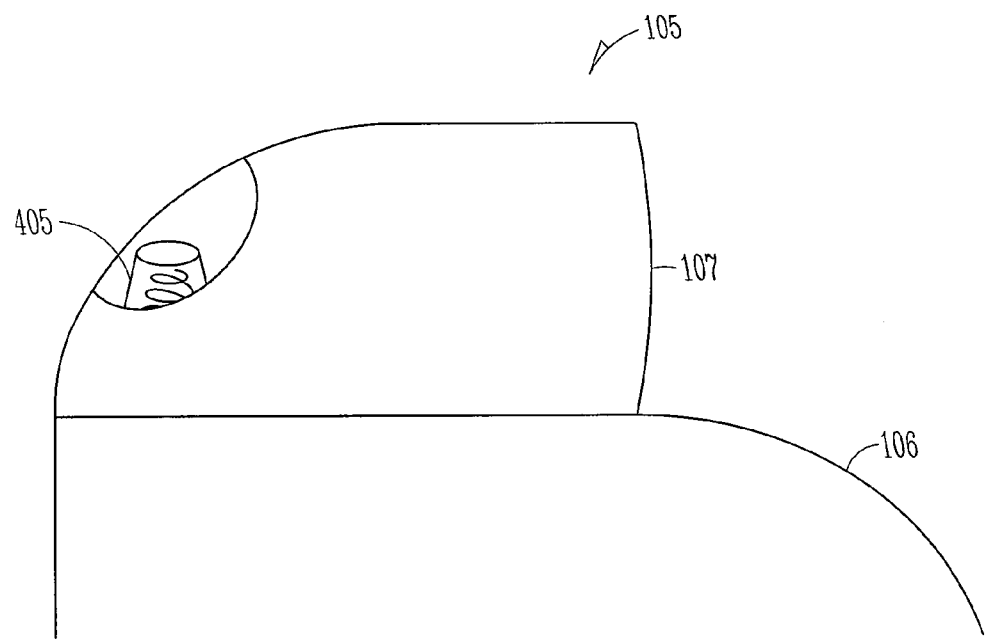
Figure 5:
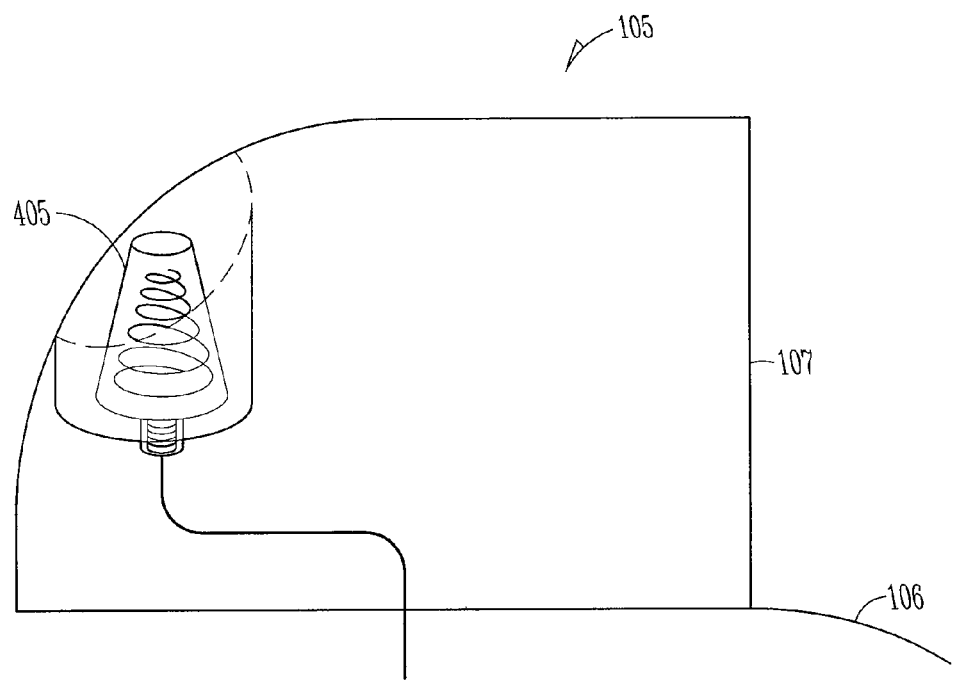

FIGS. 4 and 5 illustrate generally an example of an IMD 105 including a housing 106 and a header 107. In an example, the IMD 105 can include an antenna 405. In certain examples, the antenna 405 can include a stub helical antenna configured to be integrated into the IMD 105 (e.g., the antenna 405 can be configured to attach to the header 107).

The present inventor has recognized, among other things, that it can be advantageous to provide a convenient (e.g., manually, without requiring any special tool) attachable or detachable antenna for an implantable medical device. This can allow for separate production of the antenna and the implantable medical device. This can also allow for the attachment of different antennas for different regulatory regions or frequencies (e.g., one antenna for the MICS band and one antenna for the ISM band). In certain examples, the antenna 405 can be configured to wirelessly transfer information in a specified one of one or more of the following operating frequency ranges:

(1) a Short Range Device (SRD) band range (e.g., 862-870 MHz);

(2) a first Industrial-Scientific-Medical (ISM) band range (e.g., 902-928 MHz);

(3) a second Industrial-Scientific-Medical (ISM) band range (e.g., 2.4-2.5 GHz);

(4) a Medical Implant Communications Service (MICS) band range (e.g., 402-405 MHz); or (5) one or more other frequency band ranges configured for communication between an IMD and one or more other implantable or external devices.

The present inventor has also recognized that integration of the antenna 405 (e.g., into the header the device) can reduce the overall size of the device. The present inventor has also recognized that using a stub helical antenna allows for using a smaller package without compromising performance, further allowing the overall size of the IMD 105 to be reduced.

In the example of FIGS. 4 and 5, the antenna 405 can be configured to be integrated into an opening in the header. In certain examples, the opening in the header can be at an opposite end from a face providing one or more intravascular or other lead receptacles. This curved portion of the header can accommodate a tapered helix of decreasing diameter (in an outward direction from the housing 106), and such portion of the lead volume may be readily available for this use, in that it need not be used to provide lead receptacle bores, electrical connections, or the like.

In an example, the antenna 405 can be connected to the IMD 105 by threading or otherwise attaching the antenna 405 into a conductive connector block attached to the IMD 105 (e.g., a conductive connector block in the header 107 or the housing 106). In certain examples, the antenna 405 can be connected to the IMD 105 by directly fixing the antenna 405 to the IMD 105 (e.g., by threading the antenna 405 into the IMD 105, including into the header 107 or the housing 106), or by snapping the antenna 405 into the IMD 105 (e.g., by snapping into an undercut feature of the housing 106 or the header 107). Further, the electrical connection between the antenna 405 and the IMD 105 can use a direct electrical contact (e.g., a compression spring electrical contact) or an indirect electrical coupling (e.g., a capacitive coupling connection).

In an example, using the capacitive coupling connection can include electrically coupling the antenna 405 to an offset plane or surface in the IMD 105. The offset can be adjusted (e.g., by adjusted a distance or an angle) such as to help obtain a desired tuning of the telemetry circuit 110. In an example, the offset plane or surface can include a biocompatible conductive material insert, an integrated plated header, a plated insert, or other conductive surface. The offset plane or surface can be electrically coupled to an amplifier, a receiver, a transmitter, or other telemetry component. In an example, if the offset plane or surface is located in the header 107 and at least a portion of the telemetry circuit 110 (e.g., a receiver, a transmitter, or other telemetry component) is located in the housing 106, the offset plane or surface can be electrically coupled to the remainder of the telemetry circuit 110 using a biocompatible feed-through electrical connection from the header 107 to the housing 106.

In an example, the space in the IMD 105 where the antenna 405 attaches (e.g., the space in the header 107) can be filled, e.g., once the antenna 405 is inserted, such as for aesthetics, tuning (e.g., with a material of a desired permittivity) or the like. In certain examples, the space can be filled with a biocompatible material, such as a medical adhesive or some other biocompatible material that can be chosen, such as based on the permittivity of the material.

Figure 6:
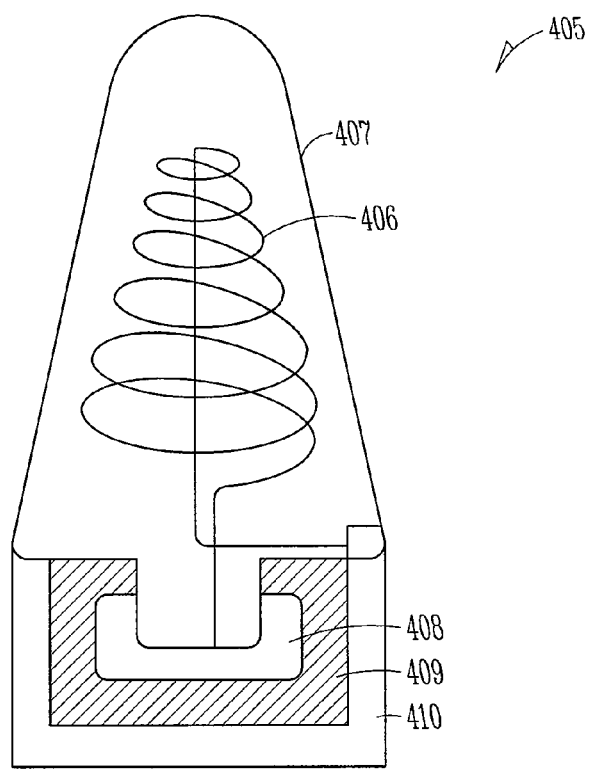
FIG. 6 illustrates generally an example of an antenna.

FIG. 6 illustrates generally an example of an antenna 405. The antenna 405 can include a helically coiled antenna 406, which can be mounted in, encapsulated in, or surrounded by an antenna overmold material 407. In certain examples, the antenna 405 can be created using a plated overmold. In an example, the helically coiled wire 406 can include one or more of a first end coupled to a first contact 408 and a second end coupled to a second contact 410. In an example, the first contact 408 can be separated from the second contact 410 such as by using an insulator 409. In certain examples, the feedwire (e.g., the conductor that couples the antenna to another portion of the telemetry circuit 110) for the first contact 408 and the second contact 410 can include a single coaxial feedwire.

In certain examples, the helically coiled antenna 406 can be loaded (e.g., at least partially filled inside of, or covered on top of or around, or any combination of at least partially filled or covered) with a material having a dielectric constant or permittivity greater than air. In an example, loading an antenna with a material having a high dielectric constant (e.g., ceramic) can modify the resonance characteristics of the radiating element. In certain examples, the loading dielectric material can increase the effective length of the antenna. In certain examples, the antenna can be loaded with a material that matches or is close to the dielectric constant of the antenna's surrounding medium (e.g., $20 \leq \in_R \leq 50$ for tissue medium or $50 \leq \in_R \leq 70$ for fluid medium).

In an example, the helically coiled antenna 406 (or other antenna capable of being similarly loaded with a high dielectric constant material, such as a spiral antenna, a cylindrical antenna, a half or quarter split cylindrical antenna, etc.) can be loaded using a polymer material having a high dielectric constant (e.g., 20-100). In an example, the polymer material can be fabricated through injection molding or other techniques.

In certain examples, another dielectric antennas configuration can be used, such as for example, a dielectric resonator antenna, a high dielectric antenna, etc.

Figure 7:
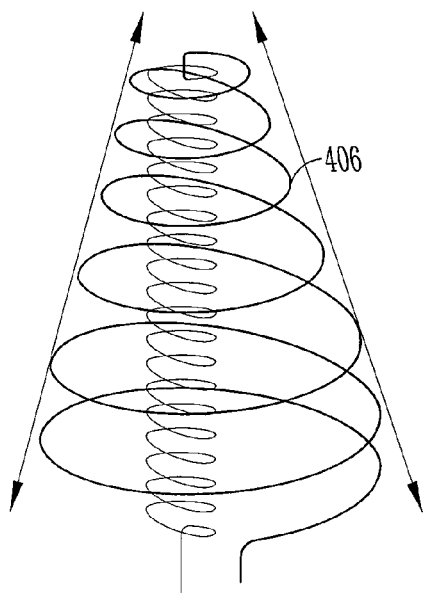
FIGS. 7, 7a, 8, and 8a illustrate generally an example of a helically coiled antenna.

FIG. 7 illustrates generally an example of a helically coiled antenna 406. The present inventor has recognized that using a balanced structure, such as the helical antenna in particular, can provide an antenna that radiates relatively consistently regardless of lead configuration, lead positioning, or header geometry, and can therefore be relatively consistent across entire product lines.

In the example of FIG. 7, the helically coiled antenna 406 can include a tapered helical configuration. In an example, the helical antenna can be tapered in order to obtain a desired shape of the overall package of the antenna 405 (e.g., to conveniently fit in the space in the curved portion of header shown in FIGS. 4 and 5), or to tune the telemetry circuit 110. In certain examples, the helically coiled antenna 406 can include more than one coil, such as a first tapered or non-tapered outer coil and one or more than tapered or non-tapered one inner coil.

Figure 7A:
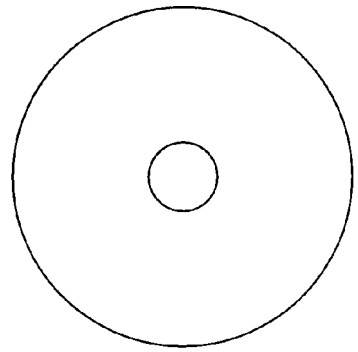

FIG. 7a illustrates generally an example of a cross sectional top view of the example of the helically coiled antenna 406 of FIG. 7.

Figure 8:
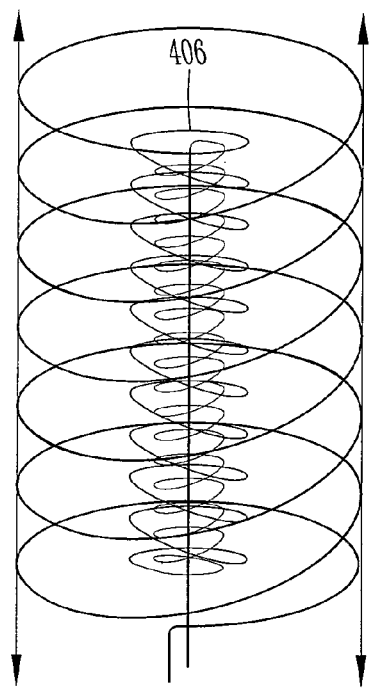

FIG. 8 illustrates generally an example of a helically coiled antenna 406 having a uniform or substantially non-tapered helix. In an example, the helical form can be uniform, such as to shape the overall package of the antenna 405 into a desired shape (e.g., to fit in the space in the header shown in FIGS. 4 and 5), or to tune the telemetry circuit 110 as desired. In certain examples, the helically coiled antenna 406 can include more than one coil, such as a first outer coil and one or more than one inner coil.

Figure 8A:
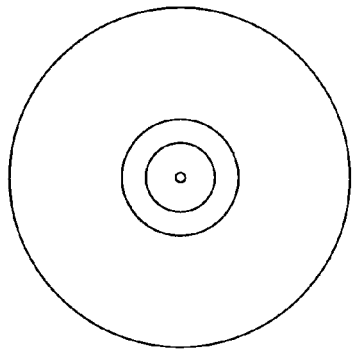

FIG. 8a illustrates generally a cross sectional top view of the helically coiled antenna 406 of FIG. 8.

In certain examples, the antenna 406 can include a printed circuit (PC) board type antenna in which an antenna can be printed or otherwise formed on or mounted to the PC board and then mounted or inserted on or into the IMD 105 (e.g., on or into the housing 106 or the header 107). In an example, an antenna layer can be printed on each side of a PC board. In certain examples, the PC board can include multiple layers, with one or more of the layers including an antenna. Either or both of the area and layer dimensions of the PC board can be used to obtain a desired two-dimensional or three-dimensional antenna structure. In certain examples, the PC board can have a first layer having a first antenna configuration configured to communicate at a first frequency and a second layer having a second antenna configuration configured to communicate at a second frequency. In certain examples, such first and second different-frequency antennas can be formed on the same layer of the PC board.

HOUSING ANTENNA EXAMPLES

Figure 9:
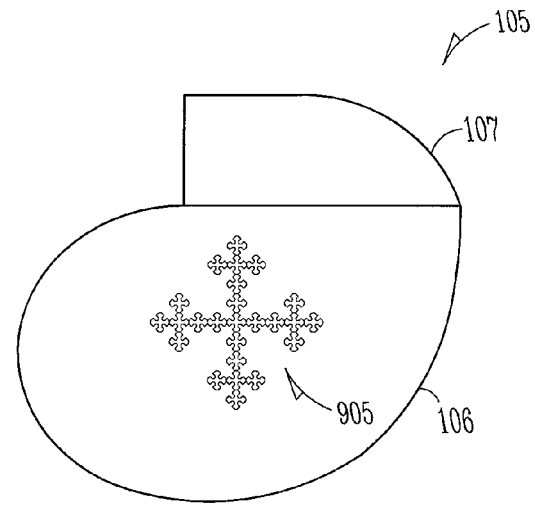
FIG. 9 illustrates generally an example of an IMD having a housing and a header.

FIG. 9 illustrates generally an example of an IMD 105 including a housing 106 and a header 107. In certain examples, the outer or inner surface of the housing 106 can include or be formed of a conductive material. In an example, at least a portion of the conductive surface of the housing 106 can be insulated and an antenna 905 can be etched, stamped, deposited or otherwise formed on the insulated layer. In certain examples, the inner or outer surface of the housing 106 can include an insulator (e.g., ceramic, plastic, etc.). If the inner or outer surface of the housing 106 includes an insulator, then the antenna 905 can be etched, stamped, deposited, or otherwise formed on the insulator.

In an example, at least a portion of the antenna 905 can be configured to be located (e.g., etched, deposited, or otherwise formed) underneath the header 107. In certain examples, at least a portion of the antenna 905 can be configured to be located on at least one of the outer surface or the inner surface of the housing 107. If the housing 107 is conductive, then it may be desirable to locate the portion of the antenna 905 on the outer surface of the housing 107, such as to avoid or reduce shielding, or to use the housing as a ground plane, if desired. In an example, the antenna 905 can include one or more of a fractal antenna, a spiral antenna, a serpentine antenna, a loop antenna, a straight wire antenna, a patch antenna, or other antenna configuration.

Further, the antenna 905 can be configured in a position or an orientation such that at least a portion of the antenna 905 can be useful as a visual or other identifier (e.g., a brand, model, bar code, etc.) for the IMD 105. In an example, a fractal antenna can be positioned to appear as an identifier (e.g., a name, number, or other signifier that can identify an individual unit, a model, a brand, a user, a patient, etc.). In certain examples, other antenna configurations can be positioned to appear as an identifier. In certain examples, the identifier can be separate from the antenna, but formed together with the antenna 905. For example, when the antenna is etched, deposited, or otherwise formed, the identifier can be concurrently etched, deposited, or otherwise formed using all or part of the process used for forming the antenna 905.

LOADED ANTENNA EXAMPLES

Generally, the length of an antenna determines the frequency the antenna is configured to transmit or receive. For example for a straight wire antenna, the antenna length should be approximately one-quarter of the desired wavelength. A loaded antenna includes an antenna (e.g., a wire antenna) that can be reactively loaded, such as by forming a coil or by placing an inductor in the length of the antenna. Placing the coil or the inductor in the length of the antenna can change the appearance or behavior of the antenna (e.g., change the impedance of the antenna, make the antenna appear electromagnetically longer, thereby allowing the antenna to be physically shorter to receive a desired frequency, etc.). The loaded antenna can be small in size, omni-directional, and it can be tuned for different frequencies or environments such as by simply adjusting or changing the inductance or location of the coil or inductor. This is in contrast to placing a coil or an inductor within a device (rather than within the antenna) to transfer or match the impedance of an antenna to the impedance of other telemetry circuit 110 components (e.g., the receiver, the transmitter, the transceiver, etc.). However, there can be a tradeoff between the physical size of the antenna and efficiency. Typically, as the length of the coil increases, the overall size of the antenna decreases, but the efficiency of the overall antenna decreases as well.

Figure 10A:
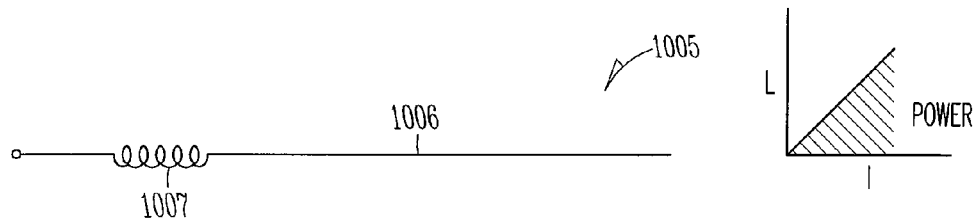
FIGS. 10a-10c illustrate generally examples of loaded wire antennas.

FIG. 10a illustrates generally an example of a base loaded wire antenna 1005. The base loaded wire antenna 1005 includes a coil 1007 at or near the base of the antenna (e.g., the base of the antenna being located at the end of the antenna that is proximal to a local transceiver electrically driving the antenna) coupled to a straight wire portion 1006. In certain examples, other types of antennas (e.g., helical, spiral, serpentine, etc.) can be base loaded using a coil or an inductor.

Figure 10B:
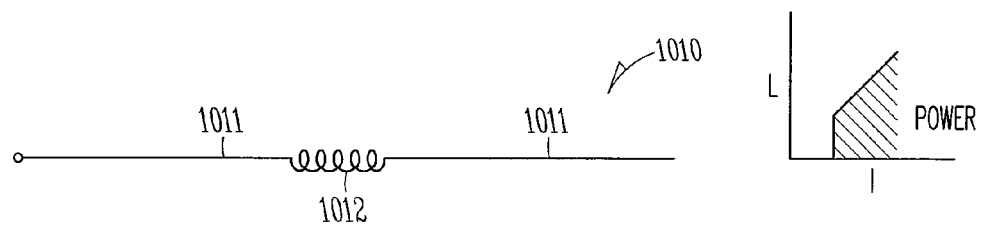

FIG. 10b illustrates generally an example of a center loaded wire antenna 1010. The center loaded wire antenna 1010 includes a straight wire length 1011 having a coil at or near the center of the antenna. In certain examples, other types of antennas (e.g., helical, spiral, serpentine, etc.) can be center loaded using a coil or an inductor.

Figure 10C:
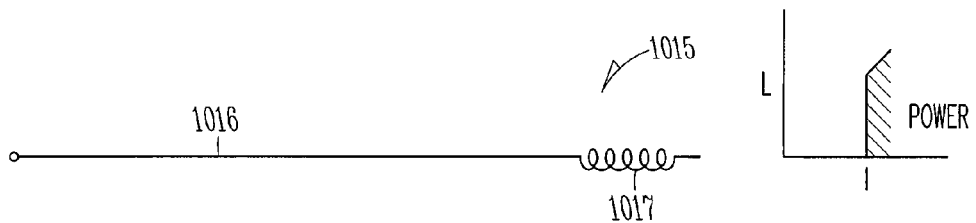

FIG. 10c illustrates generally an example of a top loaded wire antenna 1015. The top loaded wire antenna 1015 includes a straight wire length 1016 having a coil at or near the top of the antenna (e.g., the top of the antenna being located at the end of the antenna that is distal to the local transceiver electrically driving the antenna). In certain examples, other types of antennas (e.g., helical, spiral, serpentine, etc.) can be top loaded using a coil or an inductor.

The location of the coil or the inductor in the loaded antenna can affect the antenna's power profile. Generally, as the coil or the inductor is moved away from the base and toward the top of the antenna length, the power profile becomes better. By configuring the location of the coil or the inductor to be adjustable, for example, the antenna can be tuned, such as to match the RF output of the telemetry circuit 120 of the external device 115, without opening the housing 106 or adding additional components. Also, the same main assembly can be used for different frequencies because tuning can be accomplished external to the device (e.g., such as if the location of the coil or inductor is outside of the housing 106). (See generally sketches of current distribution along an antenna length across from FIGS. 10a-10c.)

Figure 11:
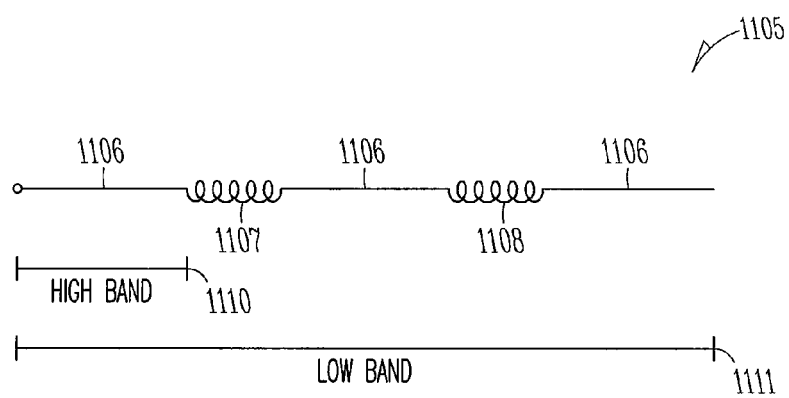
FIG. 11 illustrates generally an example of a multiband loaded antenna.

FIG. 11 illustrates generally an example of a multiband loaded antenna 1105. In certain examples, the multiband loaded antenna 1105 includes a straight wire length 1106 having one or more than one coil or inductor (e.g., more than one coil or inductor, such as the first inductor 1107 and the second inductor 1108) in its length. In certain examples, the multiband loaded antenna 1105 can include one or more other types of antennas (e.g., helical, spiral, serpentine, etc.) having one or more than one inductor.

The one or more than one coil or inductor can effectively be used to create a multiband antenna such as by blocking high frequencies along at least a portion of the length of the antenna. The frequency being blocked depends on the inductance or the location of the one or more than one coil or inductor. Generally, at high frequencies the multiband loaded antenna 1105 appears to have a first length (e.g., high band 1110). At low frequencies, the multiband loaded antenna 1105 appears to have a second length (e.g., low band 1111). Thus, the multiband loaded antenna 1105 can be tuned to operate in more than one frequency (e.g., by altering the location or value of the one or more than one inductor). In certain examples, the multiband loaded antenna 1105 can be configured with its tuning coils or inductors located so as to obtain operation in each of the MICS and ISM bands.

Figure 12:
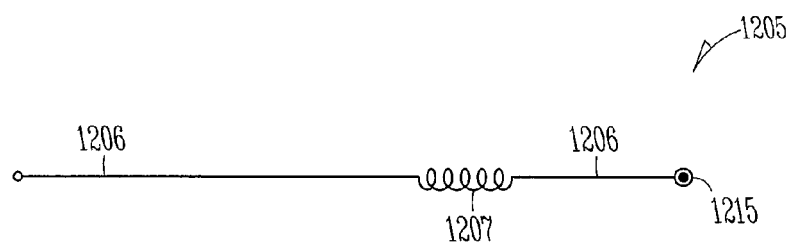
FIG. 12 illustrates generally an example of a capacitive loaded antenna.

FIG. 12 illustrates generally an example of a capacitive loaded antenna 1205. An antenna can be tuned by adding capacitance or inductance. In an example, the capacitive loaded antenna 1205 can include a straight wire length 1206 and a capacitor 1215. In an example, the capacitor 1215 can include a conductive disk or other object capable of storing a charge. In certain examples, the capacitive loaded antenna 1205 can include one or more than one inductor 1207 (e.g., configured to further tune or reduce the effective length of the capacitive loaded antenna 1205).

FIGS. 13a-13f illustrate generally an example of a loaded antenna configuration or location with respect to an IMD 105.

Figure 13A:
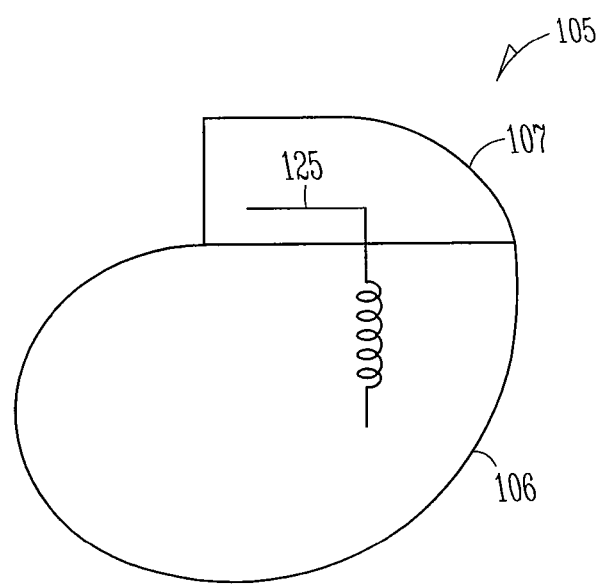
FIGS. 13a-13f illustrate generally an example of a loaded antenna configuration or location with respect to an IMD.

FIG. 13a illustrates generally an example of an IMD 105 including a base loaded antenna 125 having a coil in the housing 106 and the remainder of the base loaded antenna 125 located in the header 107. In an example, the coil (or inductor) can be shielded in the housing 106 because the loaded antenna has a majority of its radiation coming from the non-coiled portion of the loaded antenna. The non-coiled portion of the loaded antenna can be located outside of the housing 106, such as if the housing 106 is conductive so as to act as a shield. The coil can be used to tune the antenna to a desired frequency, and need not be relied upon to radiate.

Figure 13B:
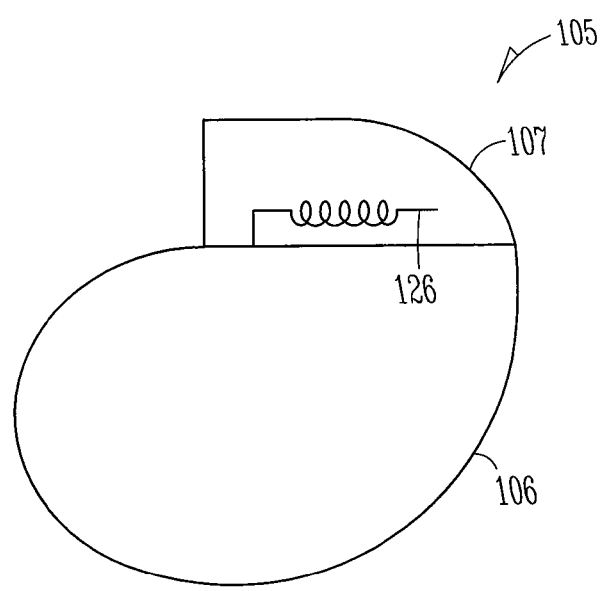

FIG. 13b illustrates generally an example of an IMD 105 including a base loaded antenna 126 having a coil and the remainder of the base loaded antenna 126 located in the header 107.

Figure 13C:
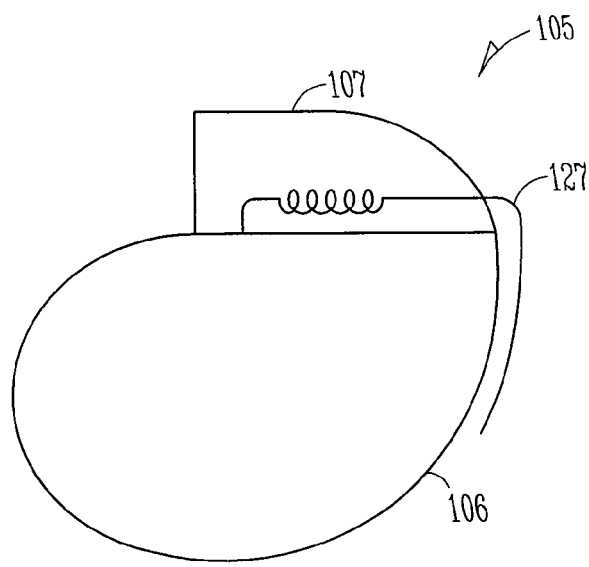

FIG. 13c illustrates generally an example of an IMD 105 including a base loaded antenna 127 having a coil located in the header 107 and the remainder of the base loaded antenna located in a combination of the header 107 and outside of the header 107 and the housing 106. In this example, the remainder of the base loaded antenna 127 can be configured to be a certain distance from the outside of the housing 106. It can be advantageous for at least a portion of the antenna to remain equidistant from the housing 106 or other conductive surface (e.g., a ground plane). In certain examples, the remainder of the base loaded antenna 127 can be configured to move away from the IMD 105 or along the header 107.

Figure 13D:
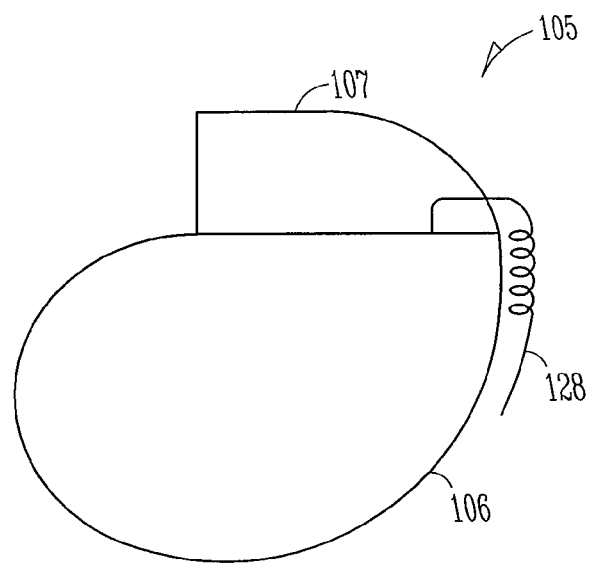

FIG. 13d illustrates generally an example of an IMD 105 including a base loaded antenna 128 having a coil and the remainder of the base loaded antenna 128 located outside of the IMD 105. In this example, the coil and the remainder of the base loaded antenna 128 can be configured to be a certain distance from the outside of the housing 106. In certain examples, the coil or the remainder of the base loaded antenna 128 can be configured to move away from the IMD 105 or along the header 107.

Figure 13E:
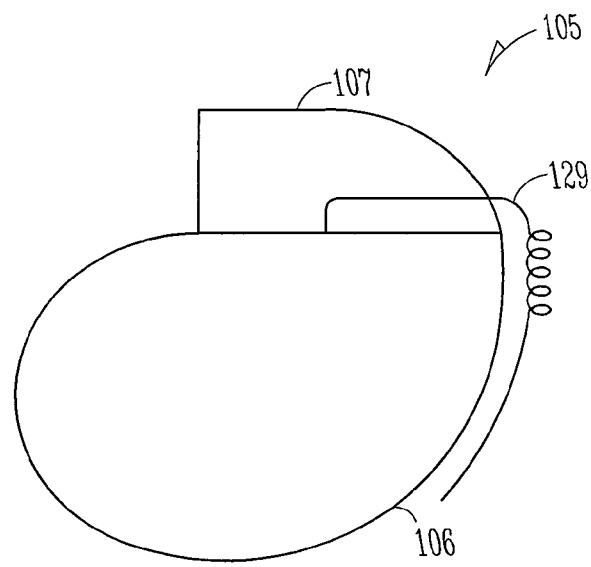

FIG. 13e illustrates generally an example of an IMD 105 including a center loaded antenna 129 having a coil located between a first and second portion of the remainder of the center loaded antenna 129. In this example, the first portion of the center loaded antenna 129 can be located in the header and the coil and the second portion of the center loaded antenna 129 can be located outside of the IMD 105 along the housing 106. In an example, the center loaded antenna 129 (including the coil and the first and second portions) can be configured to be a certain distance from the outside of the housing 106. In certain examples, the coil or the second portion of the center loaded antenna 129 can be configured to move away from the IMD 105 or along the header 107.

Figure 13F:
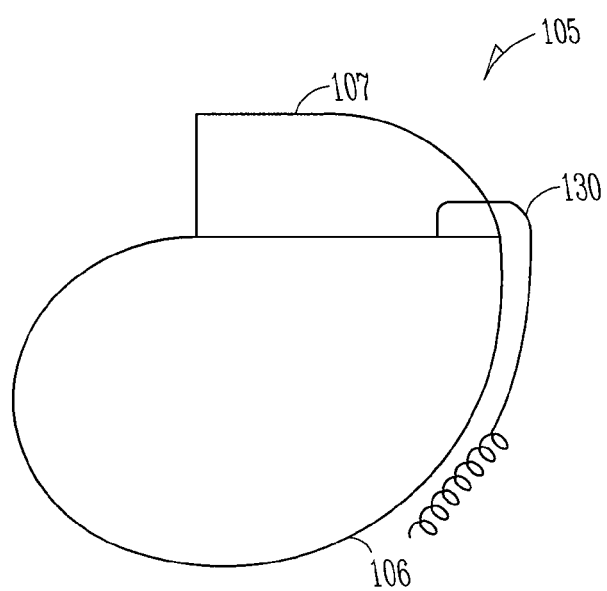

FIG. 13f illustrates generally an example of an IMD 105 including a top loaded antenna 130 having a coil and the remainder of the top loaded antenna 130 located outside of the IMD 105. In this example, the coil and the remainder of the top loaded antenna 130 can be configured to be a certain distance from the outside of the housing 106. In certain examples, the coil or the remainder of the top loaded antenna 130 can be configured to move away from the IMD 105 or along the header 107.

In the examples of FIGS. 13a-13f, at least a portion of the antennas can be separated from the outside of the housing 106, if the housing is conductive, using an insulator (e.g., molded plastic, ceramic, etc.). Further, any materials used for the antenna outside of the IMD 105 can be biocompatible or capable of being safely implanted and safely reside inside a body.

Multi-length Antenna

Generally, it is desirable not only that an antenna used for an IMD have good performance when implanted, but also that the antenna have good performance in air before the IMD is implanted. For example, it can be beneficial to establish a communication link before the IMD is implanted to test the device before implantation, to program, preprogram, or reprogram the device prior to implantation, or to otherwise communicate with the IMD prior to implantation. However, electromagnetic waves travel differently in air (having a dielectric constant of ~1) than they do in tissue (having a dielectric constant of ~50-70). One way to accommodate for this difference is to detune the antenna to have acceptable performance in both air and tissue. However, this decreases the antenna performance after implantation. In contrast to detuning the antenna, an antenna can be tuned to receive a desired frequency in more than one medium (e.g., tissue and air) having different physical characteristics (e.g., different dielectric constants).

Figure 14:
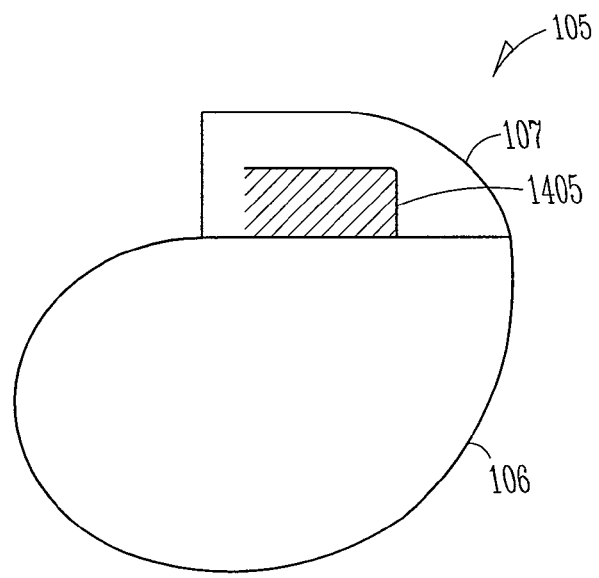
FIGS. 14-15 illustrate generally an example of an IMD including a housing, a header, and an antenna.

FIG. 14 illustrates generally an example of an IMD 105 including a housing 106, a header 107, and an antenna 1405. In this example, the antenna can be configured to have or maintain a set distance from either the housing 106 or the outer surface of the header 107. In certain examples, a ground plane can be placed between the header 107 and the housing 106.

Generally, if the antenna 1405 is placed too close to body fluid or tissue, the variations in the medium properties (e.g., the dielectric constant) or the conductivity of the tissue or body fluid can affect the performance of the antenna. Further, the radiation power of the antenna 1405 is proportionate to the area between the housing 106 and the antenna 1405. So, if the antenna 1405 is placed too close to the housing 106 (if the housing 106 includes a conductor), the radiation field will collapse. Thus, by adjusting the distance from the housing 106 and the body fluid or tissue, a point of best performance can be found.

Figure 15:
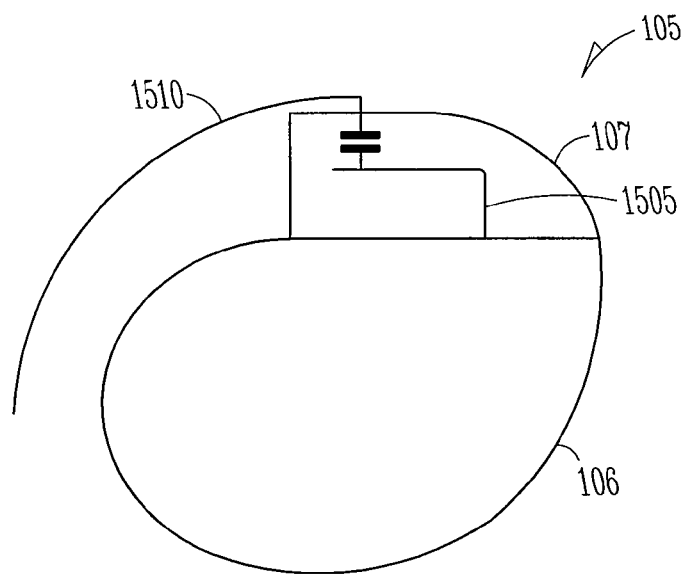

FIG. 15 illustrates generally an example of an IMD 105 having a housing 106, a header 107, a first antenna 1505, and a second antenna 1510. Generally, the desired antenna length is roughly inversely proportionate to the square root of the dielectric constant of the antenna's medium. Thus, while an antenna having a first length is optimal in a medium having a high dielectric constant (tissue~50), the optimal length in a medium having a low dielectric constant (air~1) is much longer. It can be desirable to couple a removable external antenna to the MD for in-air communication prior to or following implantation in a body.

In this example, the second antenna 1510 can include an external antenna coupled to the first antenna 1505 of the IMD 105. In an example, the second antenna 1510 can be capacitively coupled to the first antenna 1505 (or directly coupled), increasing the overall length of the combined antenna in the IMD for in-air communication. In certain examples, the second antenna 1510 can be attached to the outer surface of the IMD 105 (e.g., using an adhesive or other attachment method). The second antenna 1510 can be removed prior to implantation of the IMD 105 into a body. In certain examples, the second antenna 1510 can be a different color than the rest of the IMD 105 to draw attention, or the second antenna 1510 can include a tag with a warning label or other notification to a physician so it is not implanted with the IMD 105.

Figure 16A:
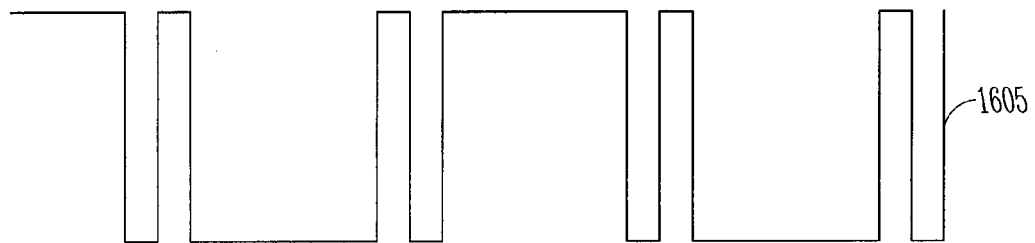
FIGS. 16a-16c illustrate generally an example of a multi-length antenna.
Figure 16B:
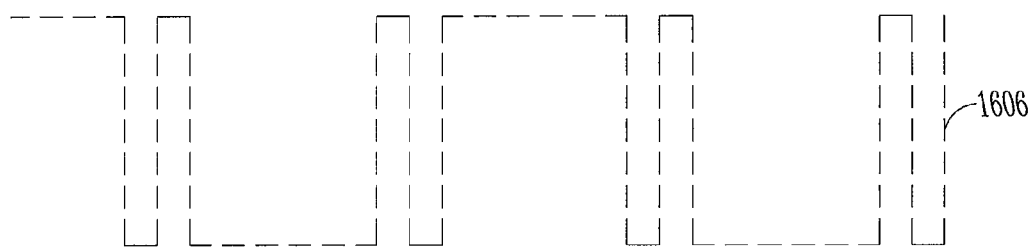
Figure 16C:
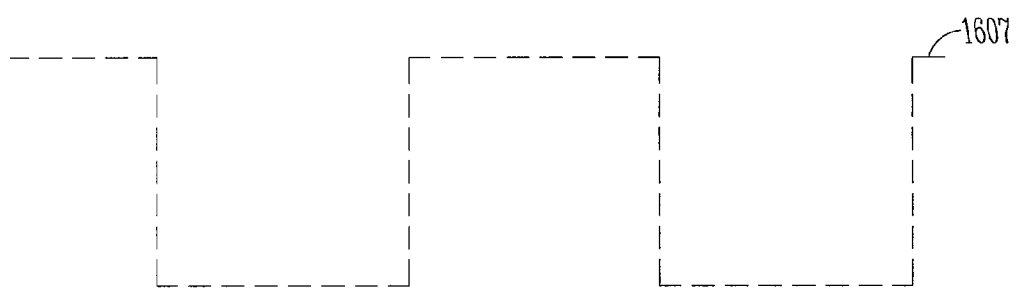

FIGS. 16a-16c illustrates generally an example of a multi-length antenna 1605. An antenna structure in a first medium having a first dielectric constant can appear electrically different than the same antenna structure in a second medium having a second dielectric constant. In an example, the multi-length antenna 1605 is configured in an antenna structure that can appear to be a first shape having a first length in a first medium, and that can appear to have a second shape having a second length in a second medium.

FIG. 16b illustrates generally an example of a first equivalent multi-length antenna 1606, or the electrical equivalent of the multi-length antenna 1605 in a medium having a low dielectric constant (e.g., air, which has a dielectric constant of about 1). In contrast, FIG. 16C illustrates generally an example of a second equivalent multi-length antenna 1606, or the electrical equivalent of the multi-length antenna 1605 in a medium having a high dielectric constant (e.g., tissue, which has a dielectric constant of about 20-50, or body fluid, which has a dielectric constant of about 50-70). In certain examples, the electrical equivalent antenna varies depending on the distance between the sections of the antenna. Thus, in a medium having a higher dielectric constant, the distance between the sections of the antenna can be farther apart and still couple, creating the shorter electrical equivalent antenna. However, in a medium having a lower dielectric constant, the distance between the sections of the antenna need to be closer together to couple. In order to have an antenna that appears to be one length in one medium and another length in another medium, the distance between the sections of antenna must be such that the coupling occurs in one medium and does not occur in the other.

Generally, there is lower capacitive coupling between two conductors in a medium having a low dielectric constant (e.g., air). Therefore, in the example of FIG. 16b, the first equivalent multi-length antenna 1606 remains similar to the original multi-length antenna 1605. In contrast, there is higher capacitive coupling in a medium having a high dielectric constant (e.g., body fluid). Thus, in the example of FIG. 16c, the second equivalent multi-length antenna 1607 is significantly different than the original multi-length antenna 1605.

In an example, the multi-length antenna 1405 can appear as a first antenna in a first medium (e.g., FIG. 16b) and a second antenna in a second medium (e.g., FIG. 16c). Therefore, one antenna can be tuned to receive a desired frequency in multiple mediums having different dielectric constants.

Figure 17:
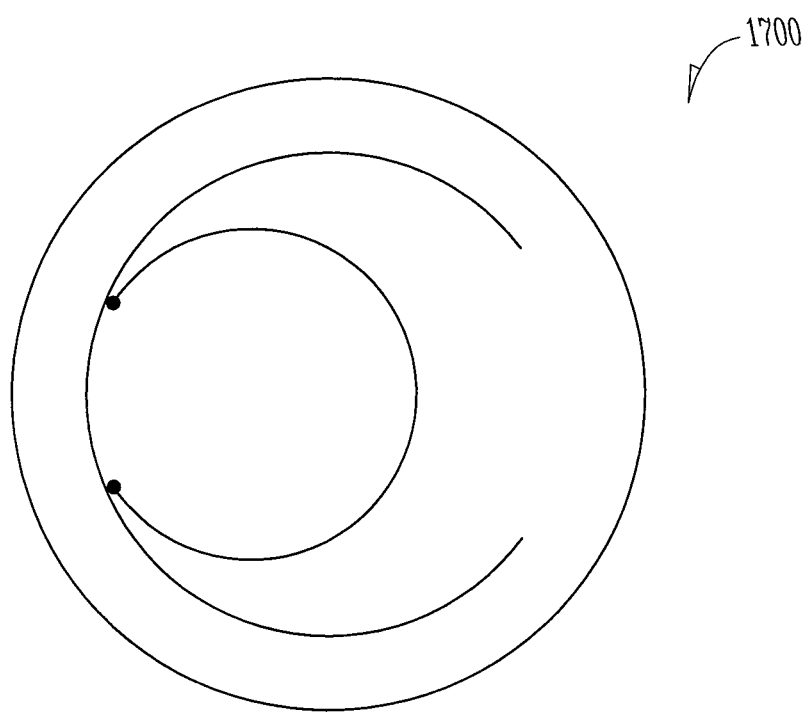
FIG. 17 illustrates generally an example of a Smith Chart illustrating the impedance of a multi-length antenna.

FIG. 17 illustrates generally an example of a Smith Chart 1700 illustrating the impedance of a multi-length antenna (similar to that shown in FIG. 16a). The two points on the chart illustrate that it can be possible to match the impedance of the antenna in the first and second mediums even though their dielectric constants are different. Matching the impedance in the first and second medium can allow for an increase in overall performance of the telemetry circuit 110.

Figure 18:
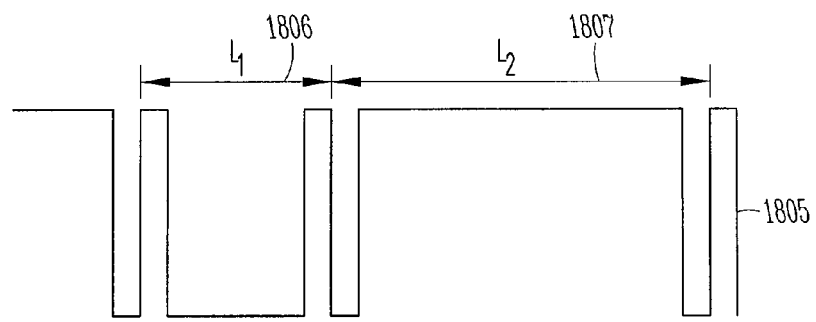
FIG. 18 illustrates generally a multi-band antenna having more than one resonant length

FIG. 18 illustrates generally a multi-band antenna 1805 having more than one resonant length (e.g., L1 and L2). In this example, the first length (L1) 1806 will resonate at a first frequency, and the antenna's second length will resonate at a second frequency.

Figure 19A:
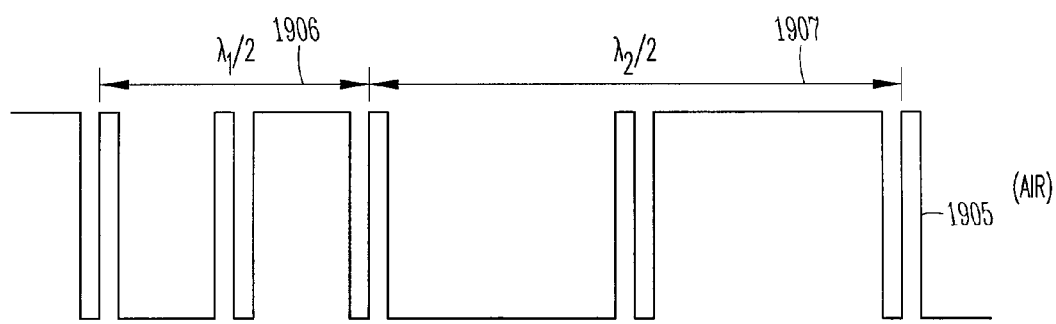
FIGS. 19a-19b illustrate generally a multi-band/multi-length antenna.
Figure 19B:
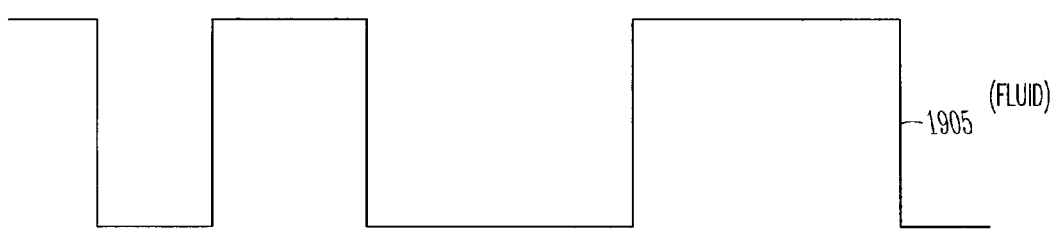

FIGS. 19a-19b illustrate generally a multi-band/multi-length antenna 1905. In the example of FIG. 19a, the multi-band/multi-length antenna 1905 appears as a first length in air and is configured to receive both a first desired frequency and a second desired frequency, depending upon the set spacing between antenna elements.

In the example of FIG. 19b, the multi-band/multi-length antenna 1905 appears as a second length in tissue or fluid and is configured to receive both a first desired frequency and a second desired frequency, depending upon the set spacing between antenna elements.

Figure 20:
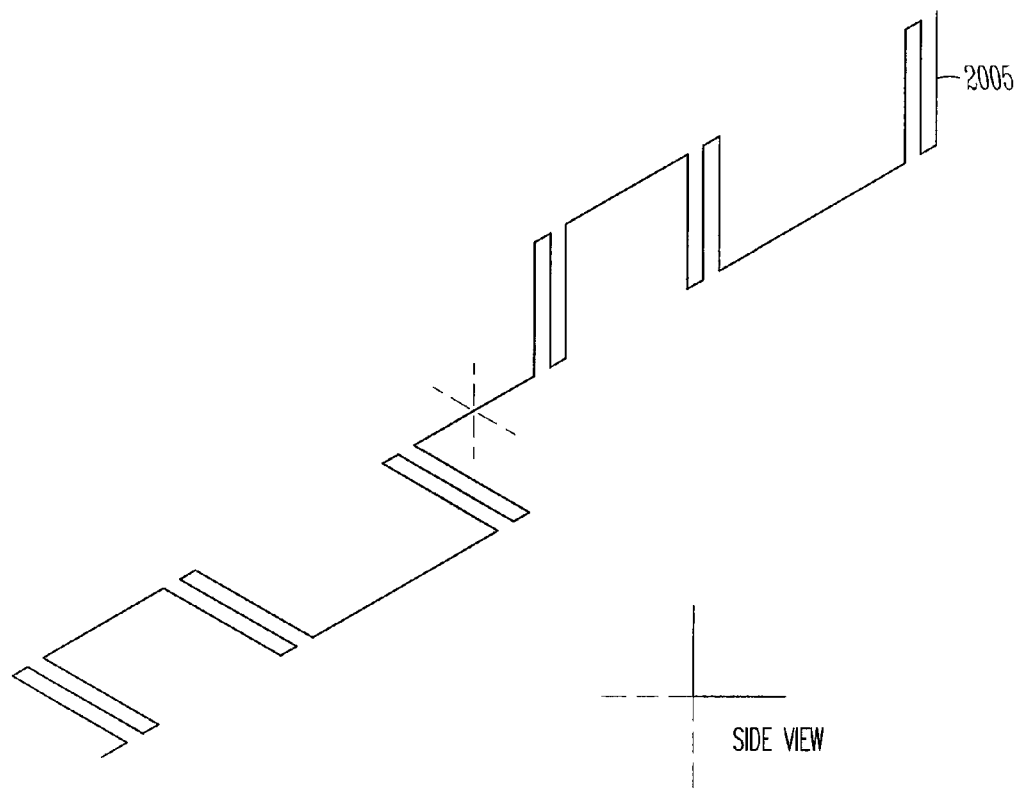
FIG. 20 illustrates generally an example of a multi-length antenna oriented along more than one axis.

FIG. 20 illustrates generally an example of a multi-length antenna 2005 oriented along more than one axis. In certain examples, the orientation of a multi-length or multi-band antenna can be changed in order to save or accommodate spatial requirements or to better direct radiation in desired directions. The example in FIG. 20 illustrates a multi-length antenna 2005 with a 90 degree change along a first axis. In other examples, other orientations, such as angles or bends other than 90 degrees or angles or bends along other axis besides that shown in FIG. 20. Further, in an example, the multi-length antenna 2005 can twist along one or more axis to further increase the direction of radiation.

Figure 21:
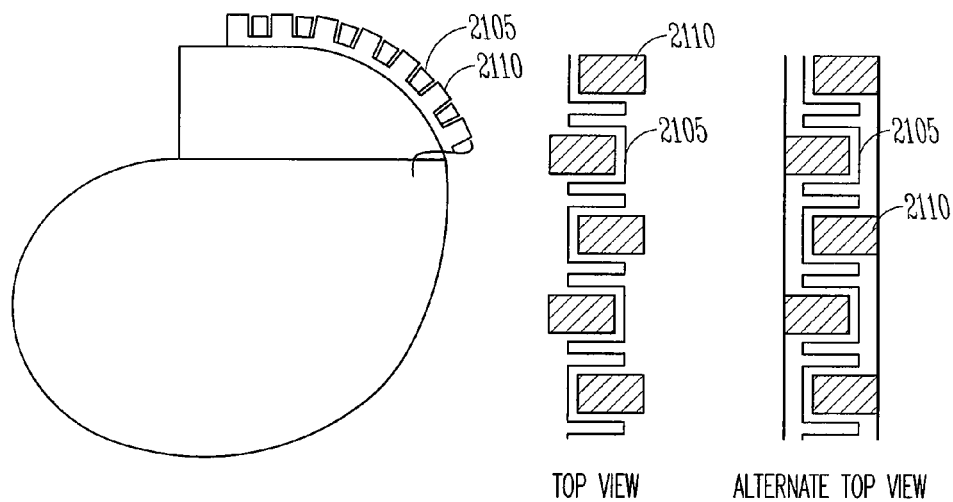
FIGS. 21-22 illustrate generally examples of a holder for an antenna.
Figure 22:
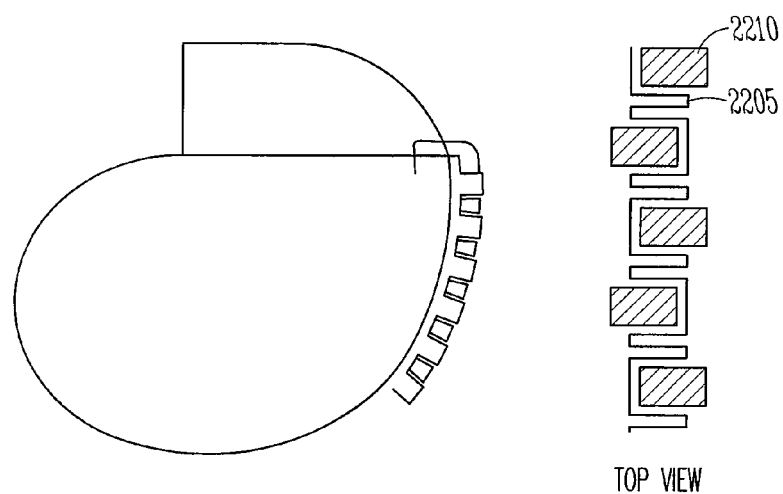

FIGS. 21-22 illustrate generally examples of a holder 2110 for an antenna 2105. In an example, the holder 2110 can be composed of a non-conductive material (e.g., plastic, etc.). Generally, the holder 2110 includes a gap running along the length of the holder 2110 in which the antenna 2105 can reside. FIG. 21 illustrates an example of the holder 2110 on the header of the IMD. FIG. 22 illustrates an example of the holder 2110 on the housing of the IMD. In certain examples, the antenna 2105 can be placed in the gap along the length of the holder 2110. In an example, the antenna 2105 can be flush along the sides of the holder 2110. In other examples, there can be space between the holder 2110 and the antenna 2105 allowing tissue or fluid to encompass, contact, or surround at least a portion of the antenna 2110. In certain examples, the dielectric value of the tissue or body fluid can assist the performance of the antenna. Generally, the closer the impedance of the antenna and the medium the antenna communicates through, the better the performance of the communication.

Figure 23A:
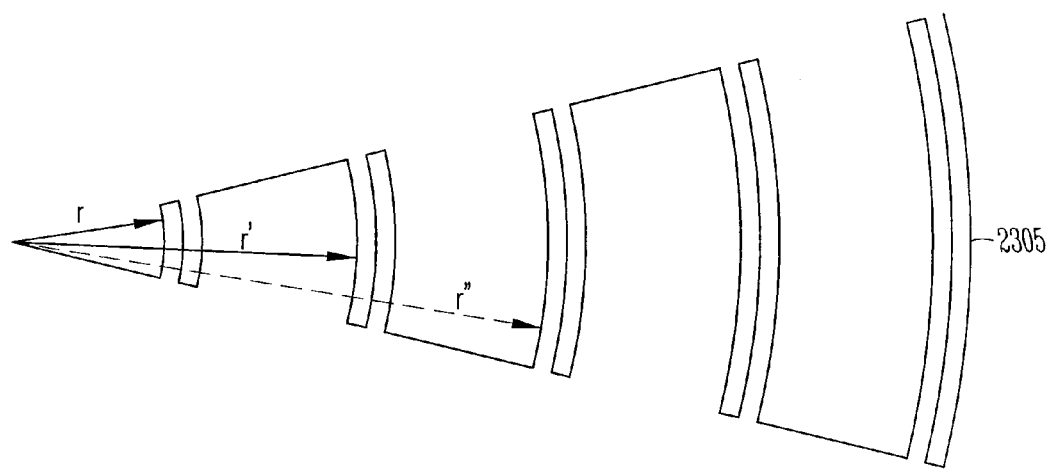
FIGS. 23a-23b illustrate generally examples of multi-length antennas.
Figure 23B:
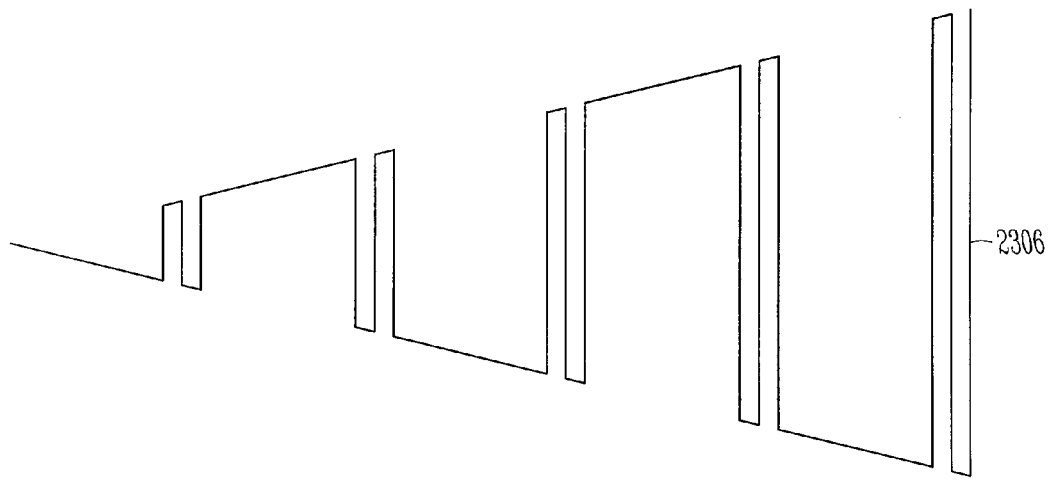

FIGS. 23a-23b illustrate generally examples of multi-length antennas. It can be advantageous to keep a first point of an antenna and a second point on the antenna as perpendicular as possible to increase radiation.

FIG. 23a illustrates generally an example of a multi-length antenna 2305 having a substantial portion of the antenna perpendicular to a first point on the antenna. Thus, the distance between the beginning of the antenna and each point along each perpendicular line is roughly equivalent.

FIG. 23b illustrates generally an example of a multi-length antenna 2306 not having a substantial portion of the antenna perpendicular to a first point on the antenna. In contrast to the antenna shown in FIG. 23a, the distance between the beginning of the antenna and each point along each perpendicular line is not roughly equivalent. Rather, the distance is greater along the ends of each perpendicular line.

Figure 24:
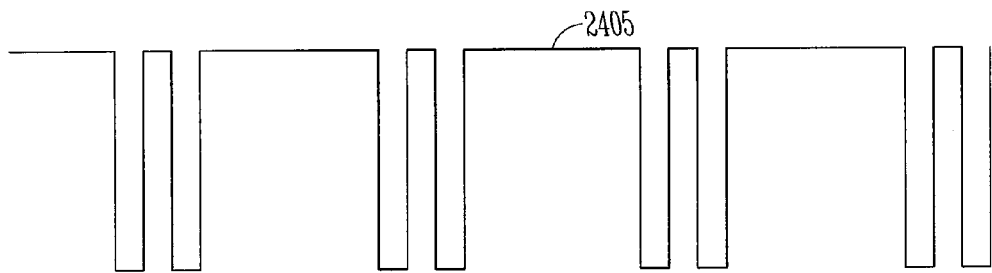
FIG. 24 illustrates generally an example of a multi-length antenna.

FIG. 24 illustrates generally an example of a multi-length antenna 2405. In this example, the multi-length antenna 2405 shares a common horizontal line amidst the remaining structure.

Figure 25:
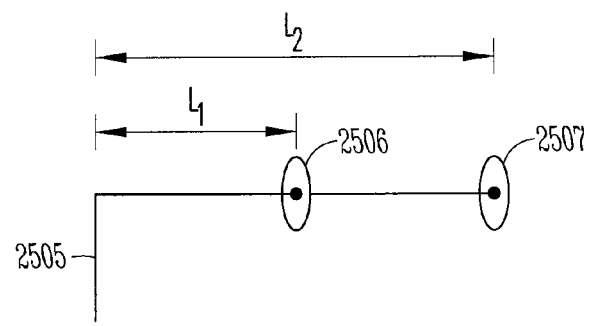
FIG. 25 illustrates generally an example of a capacitively loaded antenna having a first capacitor and a second capacitor.

FIG. 25 illustrates generally an example of a capacitively loaded antenna 2505 having a first capacitor 2506 and a second capacitor 2507. Although capacitive loading does not change the effective length of the antenna, in certain examples, capacitance can be added to an antenna in order to tune the antenna or provide a desired impedance along its surface or length.

Figure 26A:
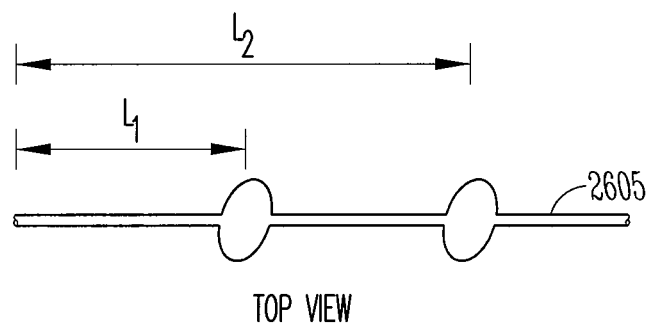
FIGS. 26a-26c illustrates generally a capacitively loaded antenna section.
Figure 26B:
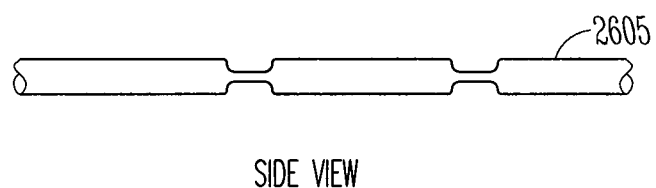
Figure 26C:
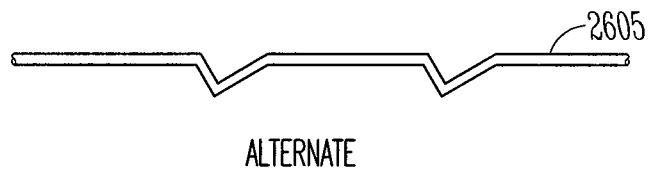

FIGS. 26a-26c illustrates generally a capacitively loaded antenna section 2605. FIG. 26a illustrates that a wire antenna (or other antenna) can be pinched in order to change the geometry or the electrical appearance of the antenna. In an example, changing the geometry or the electrical appearance of the antenna can help tune the antenna to better receive a desired frequency (e.g., increase or decrease the bandwidth or efficiency). In certain examples, pinching the antenna can result in disk-like features along the length similar to adding capacitors. FIG. 26b illustrates a side view of FIG. 26a.

FIG. 26c illustrates an alternative to pinching the antenna section. In an example, the wire antenna (or other antenna) can be smashed (or otherwise stamped), such as smashed into a crevice or other apparatus to create a sharp bend or other deformity in the antenna that changes the electrical appearance of the antenna section.

OTHER EXAMPLES

Figure 27:
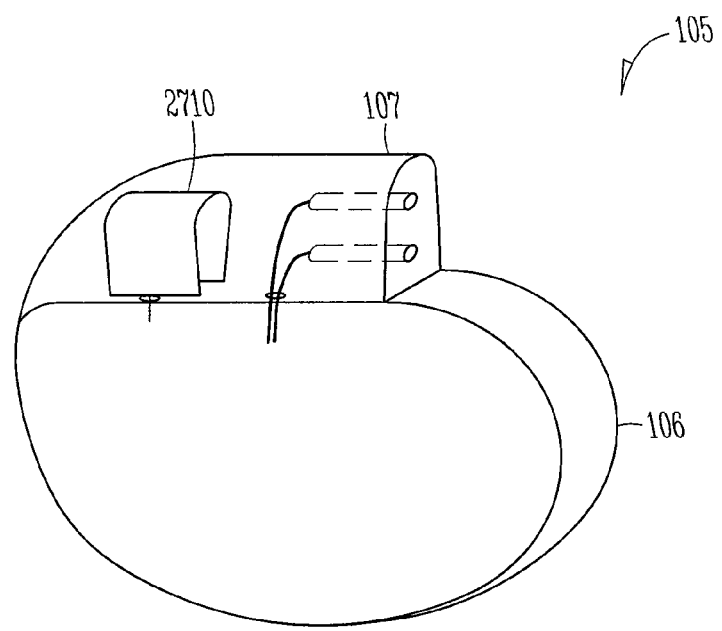
FIG. 27 illustrates generally an example of an IMD including a housing, a header, and an antenna located inside of the header.

FIG. 27 illustrates generally an example of an IMD 105 including a housing 106, a header 107, and an antenna 2710 located inside of the header 107. In an example, the antenna 2710 can include a patch antenna. Generally, a patch antenna includes a piece of metal over a ground plane. In certain examples, the patch antenna or the ground plane can be folded or curved to increase the directional coverage of the antenna.

In other examples, other types of antennas can be included in the header, such as an overmold antenna, or the header 107 itself can have a conductor placed on its outer or inner surface to use as an antenna. Generally, the overmold antenna can include a molded support having metal placed over the surface of the mold, where at least one of the support or the metal has been shaped to transmit or detect at a desired frequency.

Figure 28A:
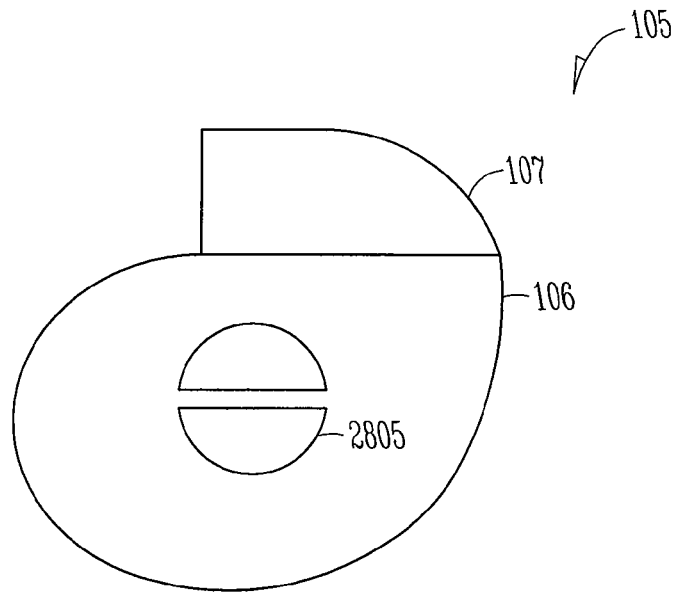
FIGS. 28a-28b illustrates generally an example of an IMD including a housing, a header, and an antenna on the surface of the housing.
Figure 28B:
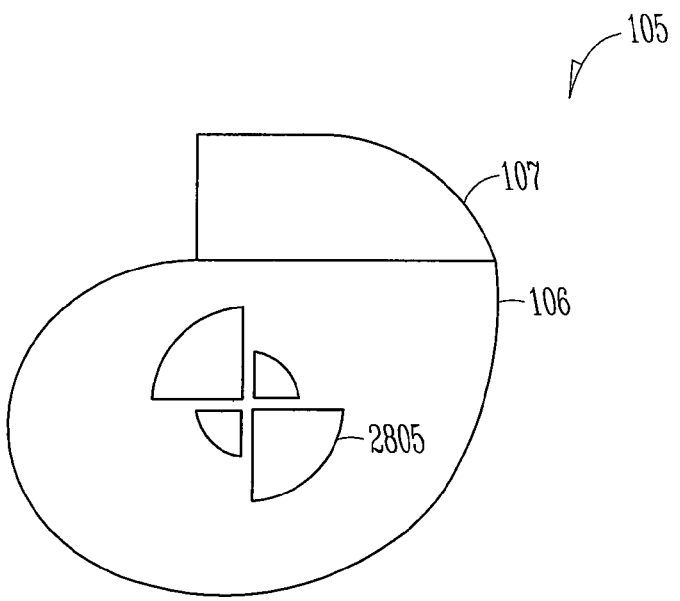

FIGS. 28a-28b illustrate generally an example of an IMD 105 including a housing 106, a header 107, and an antenna 2805 on the surface of the housing 106. In an example, the antenna 2805 (e.g., a patch antenna or other relatively flat antenna) can be placed on the exterior surface of the housing 106. If the housing 106 is conductive, then an insulator must first be put down between the antenna 2805 and the housing 106. As shown in FIG. 28a, two half-circle shaped antennas (as well as many other configurations, e.g., FIG. 28b) can be used as the antenna 2805. If the housing 106 is not conductive, then the antenna 2805 can be put directly on (or in) the surface of the housing 106. In other examples, the antenna 2805 can be placed on the inside surface of the housing 106.

Figure 29A:
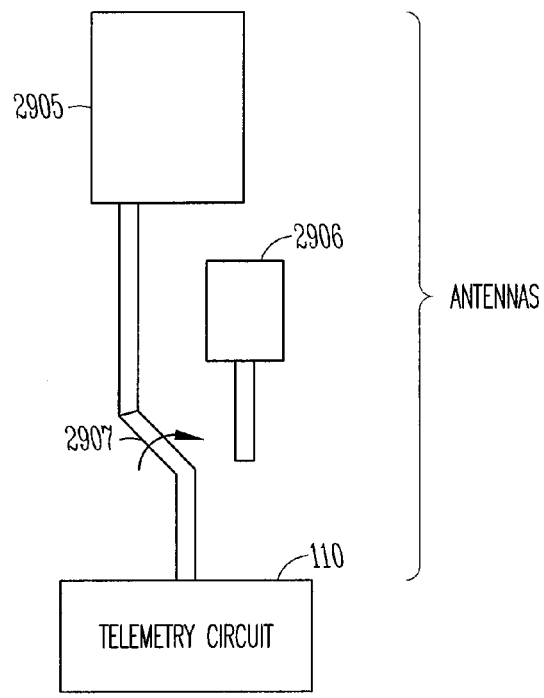
FIGS. 29a-29b illustrate generally an example of a telemetry circuit coupled to a first antenna or a second antenna.

FIG. 29a illustrates generally an example of a telemetry circuit 110 coupled to a first antenna 2905 or a second antenna 2906 through a switch 2907. In an example, the first antenna 2905 or the second antenna 2906 can include a patch antenna or other type of antenna. In certain examples, the first antenna 2905 can be tuned to a first desired frequency and the second antenna 2906 can be tuned to a second desired frequency. In other examples, the first antenna 2905 can be tuned to a desired frequency in a first medium (e.g., air) and the second antenna 2906 can be tuned to the same (or another) desired frequency in a second medium (e.g., tissue). The switch 2907 then operates to select which antenna to present to the remainder of the telemetry circuit 110. In an example, the operation of the switch 2907 can be controlled dependent upon the information received from the first antenna 2905 or the second antenna 2906. In other examples, the state of the switch is changed following or during implantation of the IMD 105. In an example, the switch 2907 continuously or periodically changes states until information is received from one antenna and not the other, or until the information received using one antenna is determined to be incorrect, noisy, or too weak to receive.

Figure 29B:
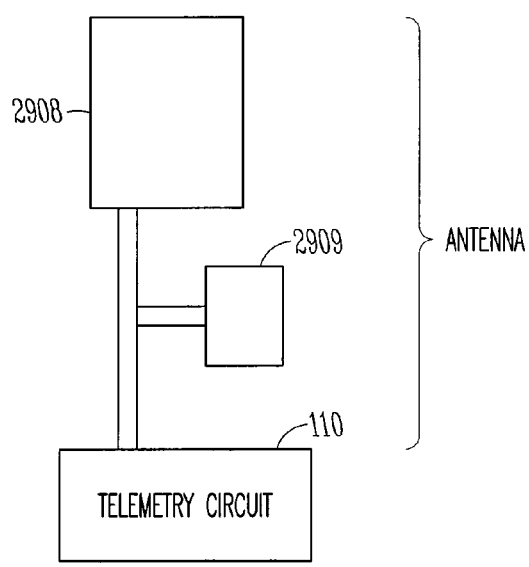

FIG. 29b illustrates generally an example of a telemetry circuit 110 coupled to a first antenna 2908 and a second antenna 2909. In this example, the telemetry circuit 110 can drive both the first antenna 2908 and the second antenna 2909. However, because the first antenna 2908 and the second antenna 2909 were either tuned for separate frequencies or for separate mediums (having different dielectric constants), one antenna resonates. In an example, the other antenna can reflect the non-resonating information. Whereas in FIG. 29a the switching occurred at the antenna, here, the determination of antenna comes from the control of the driving signal. In certain examples, the same methods regarding switching for FIG. 29a can be used to determine which frequency to drive the antennas at.

Impedance Match Tuning Networks

Figure 30:
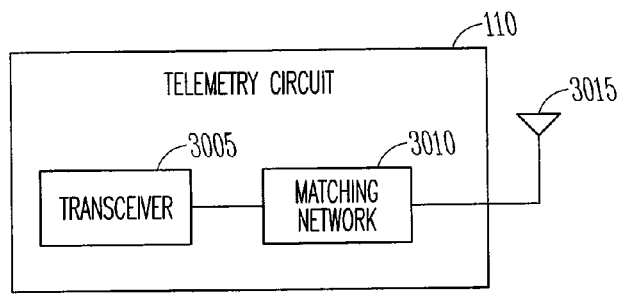
FIG. 30 illustrates generally an example of a telemetry circuit having a transceiver, a matching network, and an antenna.

FIG. 30 illustrates generally an example of a telemetry circuit 110 having a transceiver 3005, a matching network 3010, and an antenna 3015. A system and method can be used for tuning the telemetry circuit 110 impedance before or after implantation of the telemetry circuit 110 in a body. First, an impedance must be sensed or estimated. In an example, the IMD can monitor the transmitter current (a real current) to estimate the tuning of the telemetry circuit 110. In other examples, actual measurements of impedance can be made to estimate the tuning of the telemetry circuitry.

In an example, once the indication of tuning is received, the matching network 3010 can alter the impedance of the tuning circuit. FIGS. 30a-30f illustrate alternate embodiments regarding the components of the matching network.

Figure 30A:
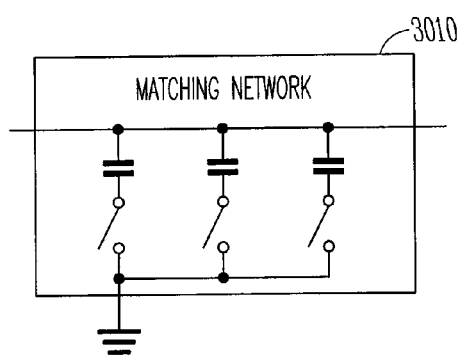
FIGS. 30a-30f illustrate alternate embodiments regarding the components of the matching network.
Figure 30B:
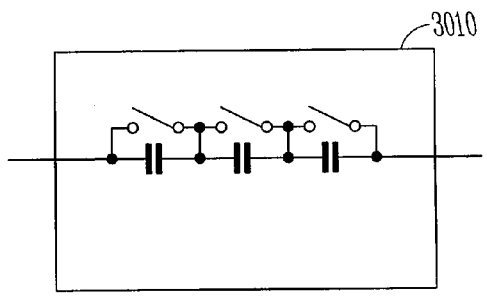
Figure 30C:
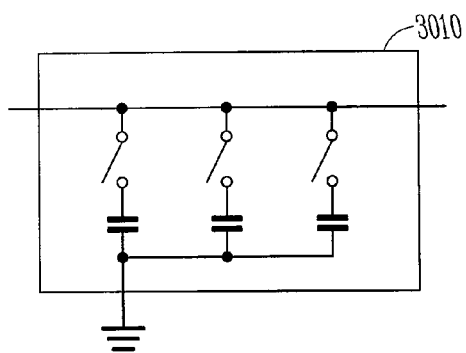
Figure 30D:
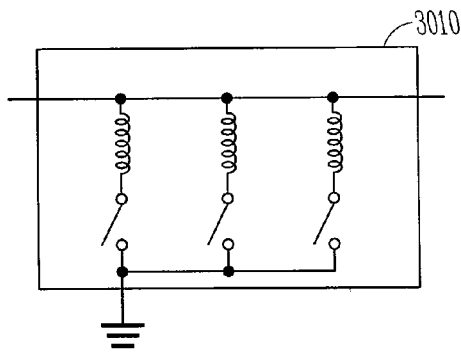
Figure 30E:
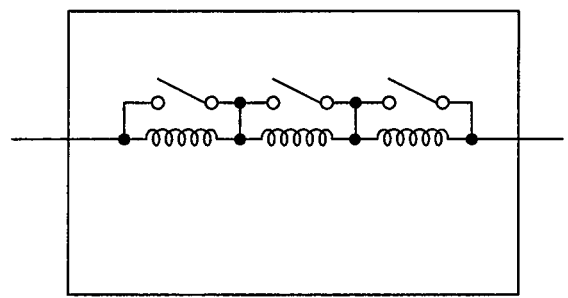
Figure 30F:
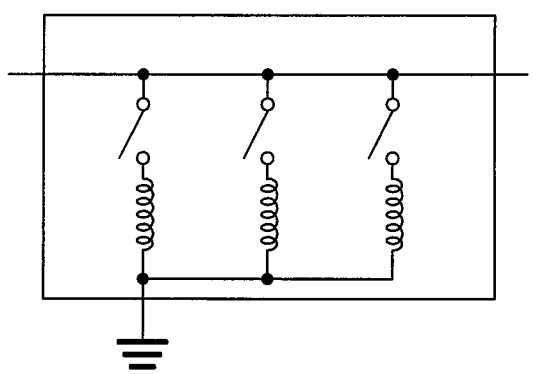

FIGS. 30a and 30c illustrate generally a matching network 3010 having switched capacitors in parallel with the transceiver 3005. FIG. 30b illustrates generally the matching network 3010 having switched capacitors in series with the transceiver 3005. FIGS. 30d and 30f illustrates generally the matching network 3010 having switched inductors in parallel with the transceiver 3005. FIG. 30e illustrates generally the matching network 3010 having switched inductors in series with the transceiver.

Transmission-line Antenna

Figure 31:
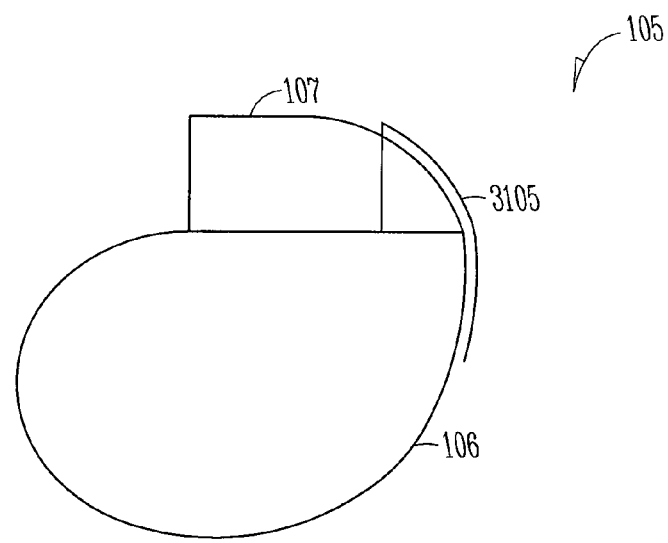
FIG. 31 illustrates generally an example of an IMD having a housing, a header, and an antenna.

FIG. 31 illustrates generally an example of an IMD 105 having a housing 106, a header 107, and an antenna 3105. In this example, the antenna 3105 can include a transmission-line style antenna (e.g., a microstrip over a ground plane, a coaxial wire, a twisted pair, etc.). However, to have an effective transmission-line antenna, the distance between the conductor and the ground plane must remain constant. If the distance varies, the electrical characteristics of the telemetry circuitry can change, which can introduce loss or poor radiation.

In the example of FIG. 31, the conductor includes a microstrip. The microstrip can be fabricated using printed circuit board (PCB) technology. In an example, the ground plane can include the housing 106. If the housing 106 is not a grounded conductor, then a ground plane can be deposited or otherwise added below or around the microstrip. In an example, the ground plane can be added using the same PCB as the microstrip conductor (e.g., using a dual sided board, using a multilayer board, etc.).

Figure 31A:
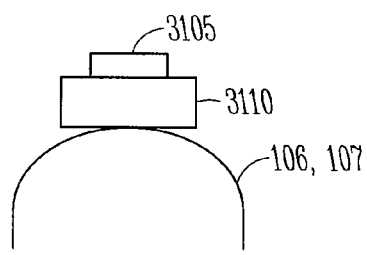
FIG. 31a illustrates generally an example of a conductor over a dielectric on the surface of the housing or the header.

FIG. 31a illustrates generally an example of a conductor 3105 over a dielectric 3110 on the surface of the housing 106 or the header 107. In certain examples, the dielectric 3110 and the conductor 3105 can be located over the header 107 and not the housing 106, the housing 106 and not the header 107, or a combination of the header 107 and the housing 106. In certain examples, the conductor 3105 over the dielectric 3110 can include a piece of metal placed over the dielectric 3110, a layer of metal deposited on the dielectric 3110, etc.

Figure 31B:
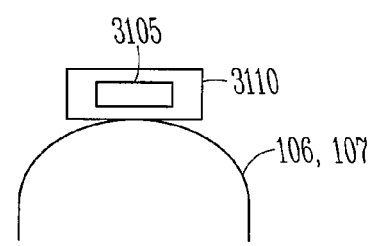
FIG. 31b illustrates generally an example of a conductor located in the middle of a dielectric on the surface of the housing or the header.

FIG. 31b illustrates generally an example of a conductor 3105 located in the middle of a dielectric 3110 on the surface of the housing 106 or the header 107. In an example, the thickness of the dielectric can be controlled during production and the distance from the housing 107 (or other ground plane) and the medium surrounding the IMD 105 (e.g., tissue or fluid) can be optimized or tuned to give a desired power at a desired bandwidth.

In an example, a lossy transmission line having a controlled and predictable impedance (the impedance changes in relation to the distance) can be preferred. In other examples, a distributed transmission line can be preferred because of the continuous structure.

In certain examples, the telemetry circuit 110 can be tuned to increase the efficiency at the cost of reducing bandwidth. By reducing the bandwidth of the telemetry circuit 110, the amount of unwanted noise (e.g., MRI noise, 60 Hz noise, or any unwanted communication or electromagnetic field) entering the IMD 105 through the telemetry circuit 110 can decrease. In other examples, other techniques can be used to not allow noise through the telemetry circuit (including the feed-through into the housing 106), such as shorting received information (e.g., transmission or noise) to the housing when the IMD 105 is not expecting to receive information. In an example, the time for receipt of information from the telemetry can be cycled so as to regularly check to receive information, but also filtering out unwanted noise for a majority of the cycle. In an example, transmission can be allowed while reception is being shorted to the housing.

Other Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
    a detachable helical antenna comprising:
    a first threaded portion;
    an electrically insulated portion coupled to the first threaded portion; and
    a conductive portion at least partially contained within the electrically insulated portion;
    wherein the detachable helical antenna is configured to use the first threaded portion to threadably engage an implantable medical device assembly;
    wherein the implantable medical device assembly includes an implantable telemetry circuit configured to wirelessly transfer information electromagnetically using the detachable helical antenna;
    wherein the detachable helical antenna includes a tapered profile having a decreasing outer radius in a direction distal to the first threaded portion; and
    wherein the conductive portion includes two or more concentric helical portions including a tapered helical portion.

2. The system of claim 1, comprising the implantable medical device assembly, wherein the implantable telemetry circuit is configured to wirelessly transfer information electromagnetically, using a specified operating frequency range, and using the detachable helical antenna; and
    wherein the specified operating frequency range includes a selected one of:
    (1) a Medical Implant Communications Service (MICS) band range extending from approximately 402 MHz to approximately 405 MHz;
    (2) a Short Range Device (SRD) band range extending from approximately 862 MHz to approximately 870 MHz;
    (3) a first Industrial-Scientific-Medical (ISM) band range extending from approximately 902 MHz to approximately 928 MHz; or
    (4) a second ISM band range extending from approximately 2400 MHz to approximately 2500 MHz.

3. The system of claim 1, wherein the two or more concentric helical portions are electrically connected in series.

4. The system of claim 1, wherein the electrically insulated portion includes a relative permittivity greater than a permittivity of air.

5. The system of claim 4, wherein the electrically insulated portion includes a ceramic material.

6. The system of claim 1, comprising the implantable medical device assembly, wherein the implantable medical device assembly includes an implantable housing comprising a conductive material, the implantable housing containing at least a portion of the implantable telemetry circuit; and
    wherein the detachable helical antenna is configured to mechanically threadably engage the implantable housing at least in part using the first threaded portion.

7. The system of claim 1, comprising the implantable medical device assembly, wherein the implantable medical device assembly includes:
    an implantable housing comprising a conductive material, the implantable housing containing at least a portion of the implantable telemetry circuit;
    a header attached to the implantable housing; and
    wherein the detachable helical antenna is configured to mechanically threadably engage the header at least in part using the first threaded portion.

8. The system of claim 7, wherein the header includes a conductive connector block electrically connected to the implantable telemetry circuit, the conductive connector block including a second threaded portion configured to receive the first threaded portion of the detachable helical antenna.

9. The system of claim 8, wherein the conductive connector block is configured to electrically connect to the implantable telemetry circuit using a capacitive connection.

10. The system of claim 8, wherein the conductive connector block is configured to electrically connect the detachable helical antenna to the implantable telemetry circuit using a first conductor in a shared feedthrough.

11. The system of claim 10, wherein the conductive connector block is configured to electrically connect a therapy signal to a therapy circuit, in the implantable medical device assembly, using a second conductor in the shared feedthrough.

12. The system of claim 7, wherein the header includes a recessed region sized and shaped to contain the detachable helical antenna entirely within the recessed region when the detachable helical antenna is mechanically threadably engaged to the header.

13. The system of claim 12, wherein the recessed region is at least partially backfilled to isolate at least a portion of the detachable helical antenna from bodily fluid or tissue when the detachable helical antenna is mechanically threadably engaged to the header.

14. The system of claim 12, comprising an overmold configured to isolate at least a portion of the detachable helical antenna from bodily fluid or tissue when detachable helical antenna is mechanically threadably engaged to the header.

15. The system of claim 7, wherein the tapered profile conforms to a profile of the header when the detachable helical antenna is fully mechanically engaged to the header.

16. A method, comprising:
    using a detachable helical antenna configured to mechanically threadably engage to an implantable medical device assembly; and
    wirelessly transferring information electromagnetically using the detachable helical antenna;
    wherein the detachable helical antenna comprises:
        a first threaded portion;
        an electrically insulated portion coupled to the first threaded portion; and
        a conductive portion at least partially contained within the electrically insulated portion;
    wherein the detachable helical antenna includes a tapered profile having a decreasing outer radius in a direction distal to the first threaded portion; and
    wherein the conductive portion includes two or more concentric helical portions including a tapered helical portion.

17. The method of claim 16, wherein the wirelessly transferring information electromagnetically using the detachable helical antenna includes wirelessly transferring information using a specified operating frequency range, the specified operating frequency range including a selected one of:
    (1) a Medical Implant Communications Service (MICS) band range extending from approximately 402 MHz to approximately 405 MHz;
    (2) a Short Range Device (SRD) band range extending from approximately 862 MHz to approximately 870 MHz;
    (3) a first Industrial-Scientific-Medical (ISM) band range extending from approximately 902 MHz to approximately 928 MHz; or
    (4) a second ISM band range extending from approximately 2400 MHz to approximately 2500 MHz.

18. The method of claim 16, comprising mechanically threadably engaging the detachable helical antenna to the implantable medical device assembly including screwing the detachable helical antenna into a threaded receiver portion of the implantable medical device assembly, the threaded receiver comprising at least one of a header, a conductive connector block, or a conductive housing.

19. The method of claim 16, comprising mechanically threadably engaging the detachable helical antenna to the implantable medical device assembly including at least one of backfilling or overmolding a recessed region of the header when the detachable helical antenna is threadably engaged to the implantable medical device and contained entirely within the recessed region.

20. The method of claim 16, wherein the wirelessly transferring information electromagnetically using the detachable helical antenna includes using a detachable helical antenna that is capacitively coupled to operate with an implantable telemetry circuit portion of the implantable medical device assembly.

* * * * *